(12) United States Patent
Wolter et al.

(10) Patent No.: US 7,897,758 B2
(45) Date of Patent: Mar. 1, 2011

(54) ACTIVATORS FOR OLIGONUCLEOTIDE AND PHOSPHORAMIDITE SYNTHESIS

(75) Inventors: Andreas Wolter, Hamburg (DE); Michael Leuck, Hamburg (DE)

(73) Assignee: Sigma-Aldrich Co., St. Louis, MO (US)

( * ) Notice: Subject to any disclaimer, the term of this patent is extended or adjusted under 35 U.S.C. 154(b) by 957 days.

(21) Appl. No.: 11/380,227

(22) Filed: Apr. 26, 2006

(65) Prior Publication Data

US 2006/0247431 A1    Nov. 2, 2006

Related U.S. Application Data

(60) Provisional application No. 60/675,135, filed on Apr. 27, 2005.

(51) Int. Cl.
C07H 21/02    (2006.01)
C07H 21/04    (2006.01)

(52) U.S. Cl. .................................... 536/25.3

(58) Field of Classification Search ........................ None
See application file for complete search history.

(56) References Cited

U.S. PATENT DOCUMENTS

| | | | |
|---|---|---|---|
| 4,474,948 A | 10/1984 | Hudson et al. | |
| 5,574,146 A | 11/1996 | Reddy et al. | |
| 6,274,725 B1 | 8/2001 | Sanghvi et al. | |
| 2007/0224616 A1* | 9/2007 | Gulari et al. | 435/6 |

FOREIGN PATENT DOCUMENTS

| WO | WO 03/004512 A1 | 1/2003 |
|---|---|---|
| WO | 2006116476 A1 | 11/2006 |

OTHER PUBLICATIONS

Vargeese et al (1998 Nucleic Acids Research 26:1046-1050).*
Nurminen, E et. al, The Effectivity of 1H-Triazoles and -Tetrazoles as Activators in Acid-Catalyzed Phosphoramidite Alcoholysis, Helvetica Chimica Acta, (2003), vol. 86, 2005-2008.
International Search Report for PCT/US06/15773, dated Sep. 13, 2006, 4 pages.
Berner et al., "Studies on the role of tetrazole in the activation of phosphoramidites", Nucleic Acids Research, 1989, vol. 17, pp. 853-864.
Beaucage et al., "Deoxynucleoside phosphoramidites—a new class of key intermediates for deoxypolynucleotide synthesis", Tetrahedron Letters, 1981, vol. 22, pp. 1859-1862.

(Continued)

*Primary Examiner*—Christopher Low
*Assistant Examiner*—Christopher M. Gross

(57) ABSTRACT

The present invention discloses novel methods for the synthesis of oligonucleotides and nucleoside phosphoramidites. The methods are based on employing aryl-substituted 5-phenyl-1H-tetrazoles with perfluoroalkyl groups on the aromatic ring as activators. In one aspect the novel activators are used in the synthesis of oligonucleotides via the phosphoramidite approach. In this aspect the activators are highly efficient and can be applied with very short coupling times. In a further aspect, the activators of the invention are used in the synthesis of phosphoramidites through the reaction of nucleosides comprising a free hydroxyl group with phosphitylating agents. In this aspect the activators provide very pure phosphoramidites under mild conditions. The activators of the invention are further characterized by being highly soluble, non-hygroscopic and non-hazardous.

16 Claims, 5 Drawing Sheets

OTHER PUBLICATIONS

Dabkowski et al., "2,4-Dinitrophenol: a novel activating reagent in nucleotide synthesis via the phosphoramidite route", Tetrahedron Letters, 2000, vol. 41, pp. 7535-7539.

Dahl et al.,"Mechanistic studies on the phosphoramidite coupling reaction in oligonucleotide synthesis", Nucleic Acids Research, 1987, vol. 15, pp. 1729-1743.

Eritja et al.,"O-Aryl Phosphoramidites: Synthesis, Reactivity and Evaluation of their use for Solid-Phase Synthesis . . . ", Tetrahedron, 1990, vol. 46, pp. 721-730.

Fourrey et al., "Improved procedure for the preparation of deoxynucleoside phosphoramidites: arylphosphoramidites . . . ", Tetrahedron Letters, 1984, vol. 25, pp. 4511-4514.

Froehler et al., "Substituted 5-phenyltetrazoles: improved activators of deoxynucleoside phosphoramidites . . . ", Tetrahedron, 1983, vol. 24, pp. 3171-3174.

Hayakawa et al., "Acid/azole complexes as highly effective promoters in the synthesis of DNA and RNA oligomers . . . ", 2003 J. Am. Chem. Soc., vol. 123, pp. 8165-8176.

McBride et al., "An investigation of several deoxynucleoside phosphoramidites useful for synthesizing . . . ", Tetrahedron Letters, 1983, vol. 24, pp. 245-248.

Pon, "Enhanced coupling efficiency using 4-dimethylaminopyridine (DMAP) and either tetrazole . . . ", Tetrahedron Letters, 1987, vol. 28, pp. 3643-3646.

Rao et al., "Use of the 1-(2-fluorophenyl)-4-methoxypiperidin-4-yl (Fpmp) protecting group in the solid phase synthesis . . . "J. Chem. Soc. Perkin Trans. I, 1993, pp. 43-55.

Tanaka et al., "Solid phase synthesis of oligoribonucleotides using o-nitrobenzyl protection of 2'-hydroxyl . . . ", Nucleic Acids Research, 1986, vol. 14, pp. 6265-6279.

Treiber et al., "A simple method for preparing pools of synthetic oligonucleotides with random point deletions", Nucleic Acids Research, 1995, vol. 23, pp. 3603-3604.

Welz et al., "5-(Benzylmercapto-)1H-tetrazole as activator for 2'-O-TBDMS phosphoramidite building blocks in RNA synthesis", Tetrahedron Lett., 2002, vol. 43, pp. 795-797.

Wright et al., "Large scale synthesis of oligonucleotides via phosphoramidite nucleosides . . . ", Tetrahedron Letters, 1993, vol. 34, pp. 3373-3376.

* cited by examiner

SEQUENCE LISTING

<160> NUMBER OF SEQ ID NOS: 14

<210> SEQ ID NO 1
<211> LENGTH: 22
<212> TYPE: DNA
<213> ORGANISM: Artificial
<220> FEATURE:
<223> OTHER INFORMATION: Deoxyribonucleotides

<400> SEQUENCE: 1
cgctcatctt caagtccacc ct                                           22

<210> SEQ ID NO 2
<211> LENGTH: 22
<212> TYPE: DNA
<213> ORGANISM: Artificial
<220> FEATURE:
<223> OTHER INFORMATION: Deoxyribonucleotides

<400> SEQUENCE: 2
agggtggact tgaagatgag cg                                           22

<210> SEQ ID NO 3
<211> LENGTH: 27
<212> TYPE: DNA
<213> ORGANISM: Artificial
<220> FEATURE:
<223> OTHER INFORMATION: Deoxyribonucleotides

<400> SEQUENCE: 3
gctcaacaca aagatgtctt ctctgtg                                      27

<210> SEQ ID NO 4
<211> LENGTH: 35
<212> TYPE: DNA
<213> ORGANISM: Artificial
<220> FEATURE:
<223> OTHER INFORMATION: Deoxyribonucleotides

<400> SEQUENCE: 4
cagtgcagct cctagcagcc tagcgtacta gtctt                             35

<210> SEQ ID NO 5
<211> LENGTH: 51

```
<212> TYPE: DNA
<213> ORGANISM: Artificial
<220> FEATURE:
<223> OTHER INFORMATION: Deoxyribonucleotides

<400> SEQUENCE: 5
cagtcctagt cacagtccag tcgctcaagc gtccagttgc acaggtcacc t            51

<210> SEQ ID NO 6
<211> LENGTH: 10
<212> TYPE: DNA
<213> ORGANISM: Artificial
<220> FEATURE:
<223> OTHER INFORMATION: Deoxyribonucleotides

<400> SEQUENCE: 6
cccccccccc                                                          10

<210> SEQ ID NO 7
<211> LENGTH: 103
<212> TYPE: DNA
<213> ORGANISM: Artificial
<220> FEATURE:
<223> OTHER INFORMATION: Deoxyribonucleotides

<400> SEQUENCE: 7
gccagccatg aaggaggagg acggccgcct gctggccagc aagtgcgtga ccgacgagtg   60
cttcttcttc gagcgcctgg agagaacaac tacaactact act                    103

<210> SEQ ID NO 8
<211> LENGTH: 10
<212> TYPE: DNA
<213> ORGANISM: Artificial
<220> FEATURE:
<223> OTHER INFORMATION: 1-9 Ribonucleotides; 10 Deoxyribonucleotide

<400> SEQUENCE: 8
uuuuuuuuut                                                          10

<210> SEQ ID NO 9
<211> LENGTH: 12
<212> TYPE: RNA
<213> ORGANISM: Artificial
<220> FEATURE:
<223> OTHER INFORMATION: Ribonucleotides

<400> SEQUENCE: 9
uacguacgua cg                                                       12

<210> SEQ ID NO 10
<211> LENGTH: 20
<212> TYPE: RNA
<213> ORGANISM: Artificial
<220> FEATURE:
<223> OTHER INFORMATION: Ribonucleotides

<400> SEQUENCE: 10
gugugugugu gugugugugu                                               20

<210> SEQ ID NO 11
<211> LENGTH: 10
<212> TYPE: DNA
<213> ORGANISM: Artificial
<220> FEATURE:
<223> OTHER INFORMATION: Deoxyribonucleotides
```

-continued

```
<400> SEQUENCE: 11
gtgtgtgtgt                                                                10

<210> SEQ ID NO 12
<211> LENGTH: 22
<212> TYPE: RNA
<213> ORGANISM: Artificial
<220> FEATURE:
<223> OTHER INFORMATION: Ribonucleotides

<400> SEQUENCE: 12
cgcucaucuu caaguccacc cu                                                  22

<210> SEQ ID NO 13
<211> LENGTH: 10
<212> TYPE: DNA
<213> ORGANISM: Artificial
<220> FEATURE:
<223> OTHER INFORMATION: Deoxyribonucleotides

<400> SEQUENCE: 13
tttttttttt                                                                10

<210> SEQ ID NO 14
<211> LENGTH: 10
<212> TYPE: DNA
<213> ORGANISM: Artificial
<220> FEATURE:
<223> OTHER INFORMATION: Deoxyribonucleotides

<400> SEQUENCE: 14
aaaaaaaaaa                                                                10
```

ACTIVATORS FOR OLIGONUCLEOTIDE AND PHOSPHORAMIDITE SYNTHESIS

RELATED APPLICATIONS

This application claims the benefit of U.S. Application Ser. No. 60/675,135, filed Apr. 27, 2005, entitled "Activators for Oligonucleotide and Phosphoramidite Synthesis", which is incorporated herein by reference in its entirety.

FIELD OF THE INVENTION

The present invention relates to the fields of nucleotide and oligonucleotide chemistry. More specifically, the invention relates to improved methods for the preparation of oligonucleotides and nucleoside phosphoramidites. In particular, the methods utilize activators which have advantages over the activators of the prior art.

BACKGROUND OF THE INVENTION

Life science research has stimulated an enormous increase in the demand for synthetic oligonucleotides over the last decades. A number of methods in molecular biology and DNA-based diagnostics to amplify, detect, analyze and quantify nucleic acids are now dependent on chemically synthesized oligonucleotides which are employed as primers and probes to amplify or to detect nucleic acid targets. Synthetic nucleic acids are also employed as active ingredients in a variety of novel therapeutics. They are used to block the expression of genes through hybridization to messenger RNA (antisense oligonucleotides), to inhibit the transcription of genes through their specific binding to transcription factors (decoy oligonucleotides), to stimulate the immune system (immunostimulatory sequences) and to bind to a variety of protein and other molecular targets due their engineered three-dimensional shape in a highly selective manner (aptamers). A particularly important and promising application is the use of short, double stranded ribonucleotides to invoke RNA interference in order to down regulate individual genes based on their sequence (siRNA). Molecular tagging of industrial products or livestock, the sequence-directed formation of nanoscale structures and molecular computing are additional important applications of synthetic oligonucleotides. Synthetic nucleic acids therefore represent a highly promising class of molecules which are very likely to have many industrial uses and to positively affect the quality of life.

Synthetic oligonucleotides are prepared through the repeated condensation of nucleosides or oligomeric nucleotide derivatives. Such condensation reactions are termed "coupling reactions". The most prominent chemical method to perform coupling reactions is the phosphoramidite approach which is displayed in Scheme 1. In this approach, a nucleotide monomer or oligomer phosphoramidite (1) is reacted with a nucleoside monomer or oligonucleotide (2) that comprises a hydroxyl group in the presence of a catalyst, termed "activator". The reaction product is a phosphorous acid triester (3) that is subsequently oxidized to a phosphoric acid triester (4). The phosphoramidite approach is largely based on developments reported by Beaucage and Caruthers (1981) Tetrahedron Letters 22:1859-1862, McBride and Caruthers (1983) Tetrahedron Letters 24:245-248, and Sinha et al. (1984) Nucleic Acids Res. 12:4539-4557, and has been reviewed by Beaucage and Iyer (1992) Tetrahedron 48:2223-2311, each of which is incorporated herein by reference in its entirety.

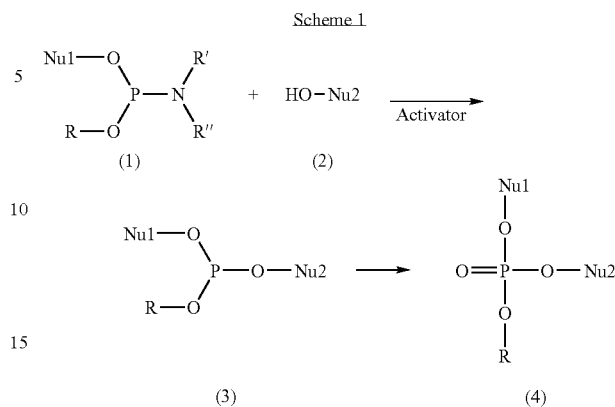

wherein

Nu1, Nu2=monomeric or oligomeric nucleoside/nucleotide groups;

R=phosphate protective group, e.g. β-cyanoethyl; and

R', R"=alkyl groups, e.g. diisopropyl.

Coupling reactions are either performed in solution or with the nucleoside monomer or oligonucleotide (2) being immobilized on a solid support (solid phase oligonucleotide synthesis=SPOS), which is the preferred method for the synthesis of oligonucleotides. In SPOS oligonucleotides are assembled in a cyclical manner, each cycle consisting of a series of three chemical reactions. The first reaction is a deblocking reaction, i.e. the removal of a front-end protective group from the nucleoside or oligonucleotide bound to the support, for example the removal of a dimethoxytrityl protective group. The second reaction is the coupling reaction of a nucleotide monomer or oligomer phosphoramidite to the partially deprotected nucleoside or oligonucleotide on the support in the presence of an activator. The third reaction is the oxidation of the phosphite triester coupling product to a phosphate triester. Optionally, a capping reaction is included in each cycle either directly before or after the oxidation reaction in order to block those support bound nucleosides or oligonucleotides which failed to react in the coupling reaction and to prevent them from further growth in subsequent chain elongation steps.

One of the major methods of preparing phosphoramidites (1) is to react a nucleoside (5) with a phosphitylating agent (6) in the presence of a catalyst, as displayed in Scheme 2. The catalyst applied in this process is termed an "activator" analogous to the catalyst applied in the synthesis of oligonucleotides mentioned above.

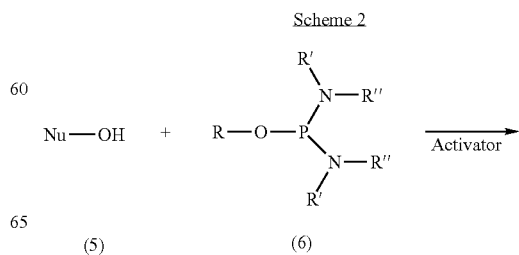

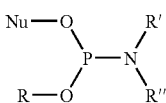

wherein

Nu=monomeric or oligomeric nucleoside/nucleotide group;

R=phosphate protective group, e.g. β-cyanoethyl; and

R', R"=alkyl groups, e.g. diisopropyl.

Several compounds have been described as activators for the synthesis of oligonucleotides via the phosphoramidite approach in the technical literature, most of them being either azoles or azolium salts formed from azoles with strong acids, e.g. azolium triflates. The common feature of the described activators is that they represent weak proton acids as well as good nucleophiles (the nucleophile being either the respective compound itself or its conjugated base). Both functions, i.e. providing a weak proton acid and a nucleophile, are deemed important in the mechanism of phosphoramidite coupling reactions as discussed by Dahl et al. (1987) Nucleic Acids Res. 15:1729-43, and Berner et al. (1989) Nucleic Acids Res. 17:853-864, each of which is incorporated herein by reference in its entirety. Activators for the synthesis of oligonucleotides are also applied as activators for the synthesis of phosphoramidites. Ammonium salts of azoles, e.g. the diisopropylammonium salts of 1H-tetrazole or 4,5-dicyanoimidazole, are also used for this purpose.

A number of activators are being marketed commercially for the synthesis of oligonucleotides. Examples of commercially available activators include 1H-tetrazole, described by Beaucage and Caruthers (1981) Tetrahedron Letters 22:1859-1862, 4,5-dicyanoimidazole ("DCI"), described by Vargeese et al. (1998) Nucleic Acids Res. 26:1046-1050, 5-ethylthio-1H-tetrazole ("ETT"), described by Wright et al. (1993) Tetrahedron Letters 34:3373-3376, and 5-benzylthio-1H-tetrazole ("BTT"), described by Welz and Muller (2002) Tetrahedron Letters 43:795-797. Each of these references is specifically incorporated herein by reference in its entirety.

Other activators that have been described in the literature include 5-(4-nitrophenyl)-1H-tetrazole, described by Froehler and Matteucci (1983) Tetrahedron Letters 24:3171-3174, 5-(3-nitrophenyl)-1H-tetrazole, described by Rao et al. (1993) J. Chem. Soc. Perkin Trans. I 43-55, N-methylanilinium trifluoracetate, described by Fourrey and Varenne (1984) Tetrahedron Letters 25:4511-4514, 2,4-dinitrophenol, described by Dabkowski et al. (2000) Tetrahedron Letters 41:7535-7539, 1-hydroxybenzotriazole, described by Eritja (1990) Tetrahedron 46:721-730, 2,4-dinitrobenzoic acid, described by Reddy and Farooqui., U.S. Pat. No. 5,574,146, benzimidazolium triflate and other azolium salts, e.g. N-phenylimidazolium triflate, described by Hayakawa et al. (1996) J. Org. Chem. 61:7996-7997 and (2001) J. Am. Chem. Soc. 123:8165-8176, 1,2,3-benzotriazole and 5-substituted derivatives thereof, described by Hudson and Cook, U.S. Pat. No. 4,474,948, pyridinium hydrochloride, described by Gryaznov and Letsinger (1992) Nucleic Acids Res. 20:1879-1882, 1-methyl-5-mercaptotetrazole, described by Efimov et al. (1996) Russ. J. Bioorg. Chem. 22:128-130, a combination of pyridinium trifluoracetate and 1-methylimidazole, described by Sanghvi and Manoharan, U.S. Pat. No. 6,274,725, saccharin, described by Sinha and Revell, International Publication No. WO 03/004512, and other compounds. Each of these references is specifically incorporated herein by reference in its entirety.

The activators described to date have certain disadvantages that warrant the search for new and improved activator molecules. For instance, some of the described activators are hygroscopic, such as pyridinium chloride, which requires very strict exclusion of moisture for their storage and handling. The application of such activators in the synthesis of oligonucleotides results in a high risk for synthesis failure due to the great sensitivity of coupling reactions with respect to moisture. This risk is particularly pronounced when a low molar excess of phosphoramidite is applied, for instance in large scale solid phase oligonucleotide synthesis or in coupling reactions which are performed in solution.

Other activators are sensitive to heat and/or mechanical impacts and may cause explosions under such conditions, e.g. 1H-tetrazole and ETT. 1H-Tetrazole tests positive in a test of mechanical sensitivity with respect to shock ("Fallhammertest"), and is classified as a Category A explosive in Germany. ETT is classified as a Category C explosive in Germany due to its thermal sensitivity. These activators, when used as powders, require special handling and safety procedures during their purification, storage, shipping, use and disposal which increases the cost in routine applications. They also raise safety concerns as they may cause great damage to personnel, equipment and buildings under special conditions, e.g. in case of a fire, when stored in large quantities.

Other activators such as 5-(4-nitrophenyl)-1H-tetrazole (7) have low solubility in acetonitrile, the preferred solvent for coupling reactions, and may crystallize in the lines and valves of automated oligonucleotide synthesis instruments upon slight variations of the environmental temperature, thus blocking the instrument and causing synthesis failures. This undesired phenomenon also occurs with 1H-tetrazole, which is routinely applied at concentrations near its maximum solubility in acetonitrile (appr. 0.45 M at 25° C.).

(7)

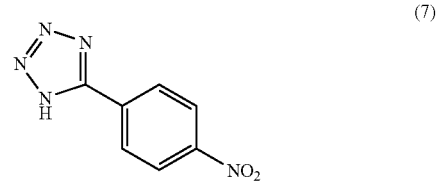

Other activators, like DCI, may cause precipitation and associated line clogging or valve failure in certain DNA/RNA synthesis instruments due to the incompatibility of solutions of these activators in acetonitrile with other synthesis solutions applied in such instruments. For instance, a mixture consisting of 10 volume percent of a 0.5 M DCI-solution in acetonitrile and 90 volume percent of a 3% solution of trichloroacetic acid in dichloromethane (w/v) becomes cloudy instantaneously after mixing of the two components and a precipitate is deposited from the resulting suspension. It appears likely that such precipitation is caused by the low solubility of DCI in dichloromethane. A solution of 3% trichloroacetic acid in dichloromethane is widely applied in DNA/RNA synthesis instruments for the removal of dimethoxytrityl protective groups in the deblocking reaction of SPOS cycles. The deblocking reaction is immediately followed by the coupling reaction in an SPOS cycle, thus causing a risk of precipitate forming in the machine, because the employed activator solution may come in direct contact with the solution employed in the deblocking reaction.

In the field of phosphoramidite-mediated RNA synthesis, the activators described so far are generally not active enough to promote coupling efficiencies comparable to those observed in DNA synthesis. This phenomenon especially relates to the most widely used RNA amidites, i.e. 2'-O-tert-butyl-dimethylsilyl protected RNA amidites. With existing activators these amidites require longer coupling times at higher activator and/or amidite concentration, but still result in inferior product yields and purity compared to DNA synthesis. Consequently, it is desirable to develop alternative activators that promote the highly efficient synthesis of RNA oligonucleotides.

Although, as discussed above, a variety of activators for the synthesis of oligonucleotides and phosphoramidites have been described, and some of the described activators are commercially available, there is a need to find improved activators that combine the desired features of high activation efficiency and good solubility with easy, safe and economic handling, which lead to superior synthesis results. In particular, the synthesis of RNA oligonucleotides and other oligonucleotides prepared from sterically demanding phosphoramidites requires more efficient activators than are currently available.

The present invention discloses novel methods and activators for the synthesis of oligonucleotides and nucleoside phosphoramidites based on aryl substituted 5-phenyl-1H-tetrazoles wherein at least one of the substituents on the aromatic ring is a perfluoroalkyl substituent. The disclosed activators are highly efficient in coupling DNA-, RNA- and other phosphoramidites, highly soluble, non-hygroscopic and non-hazardous.

SUMMARY OF THE INVENTION

The present invention discloses novel methods for the synthesis of oligonucleotides via the phosphoramidite approach. Included in the present invention are novel methods for the synthesis of phosphoramidites. The methods are based on the application of novel aryl-substituted 5-phenyl-1H-tetrazoles as catalysts in coupling reactions of the phosphoramidite approach for the synthesis of oligonucleotides and in the synthesis of phosphoramidites with phosphitylating agents.

In one embodiment, the present invention discloses novel methods for the synthesis of oligonucleotides via the phosphoramidite approach, wherein the coupling reaction is performed in the presence of certain aryl-substituted 5-phenyl-1H-tetrazoles as catalysts. The catalysts employed in the methods of the invention are characterized by carrying perfluoroalkyl substituents on the phenyl ring and can be represented by the following general structure:

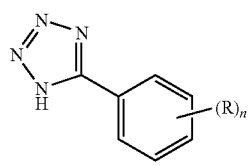

(13)

wherein R is as defined below and wherein at least one R contains a perfluoroalkyl substituent and wherein n is an integer selected from 1-5. These catalysts are highly soluble in the solvent of the coupling reaction and promote the highly efficient synthesis of DNA, RNA and modified oligonucleotides. In one preferred embodiment the aryl-substituted 5-phenyl-1H-tetrazole is 5-(3,5-bis(trifluoromethyl)phenyl)-1H-tetrazole (8).

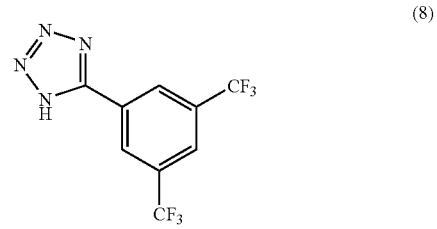

(8)

In one embodiment of the invention the synthesis of oligonucleotides is conducted as solid phase oligonucleotide synthesis (SPOS). In a preferred embodiment, the synthesis of oligonucleotides is conducted as solid phase oligonucleotide synthesis and the aryl-substituted 5-phenyl-1H-tetrazole is 5-(3,5-bis(trifluoromethyl)phenyl)-1H-tetrazole (8).

Using the method of this invention, the coupling time employed in the synthesis of DNA oligonucleotides is shorter than the coupling time employed in the conventional methods in the art. In preferred embodiments, the maximum coupling time for DNA phosphoramidites is about 15 seconds and the maximum coupling time for 2'-O-tert-butyldimethylsilyl RNA phosphoramidites is about 5 minutes.

In other embodiments, the novel activators of the invention are applied in the presence of a nucleophilic catalyst. In a preferred embodiment, the nucleophilic catalyst is N-methylimidazole.

In another embodiment, the present invention discloses novel methods for the synthesis of nucleoside phosphoramidites through the reaction of a nucleoside comprising a free hydroxyl group with a phosphitylating agent in the presence of aryl-substituted 5-phenyl-1H-tetrazoles as catalysts wherein the substituents on the phenyl ring are perfluoroalkyl substituents.

In a preferred embodiment the synthesis of phosphoramidites is conducted in the presence of 5-(3,5-bis(trifluoromethyl)phenyl)-1H-tetrazole (8) as catalyst. In another preferred embodiment the synthesis of phosphoramidites is conducted employing bis(diisopropylamino)-2-cyanoethoxyphosphane as phosphitylating agent.

In a particularly preferred embodiment, the synthesis of phosphoramidites is conducted in the presence of 5-(3,5-bis(trifluoromethyl)phenyl)-1H-tetrazole (8) as catalyst and bis(diisopropylamino)-2-cyanoethoxyphosphane is employed as phosphitylating agent.

Additional objectives and advantages of the present invention will be apparent to those skilled in the art upon examination of the detailed description that follows.

DETAILED DESCRIPTION OF THE PREFERRED EMBODIMENT

Figure 1A:
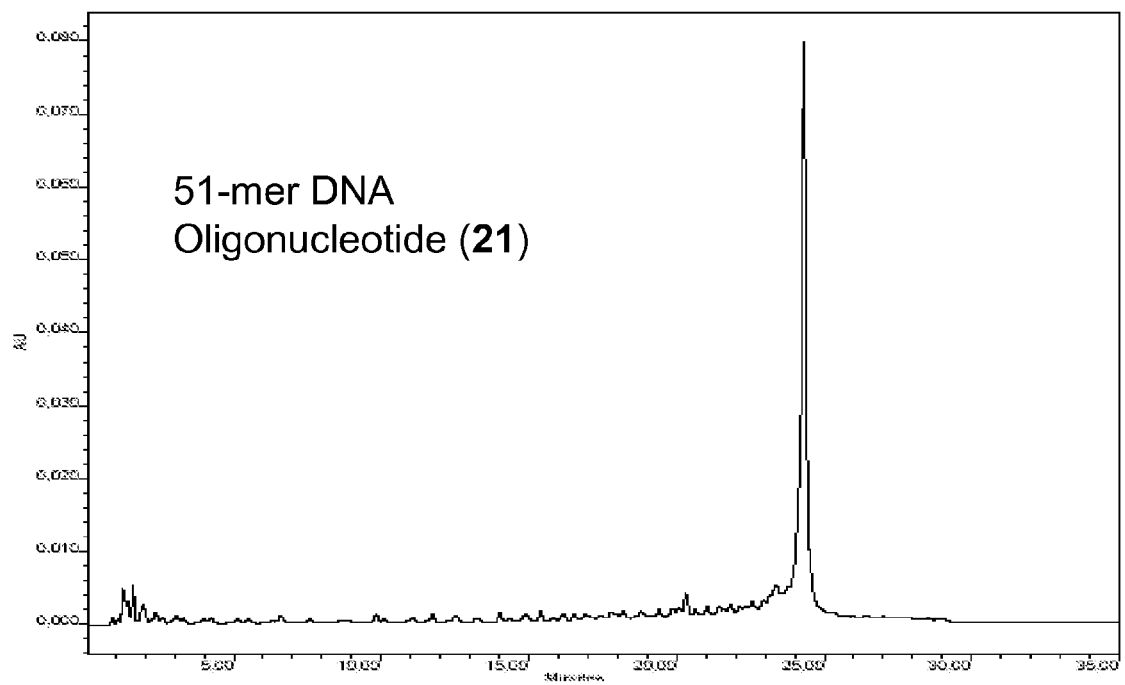
FIGS. 1A and 1B display the anion exchange chromatograms of the 51-mer DNA oligonucleotide product (21) and the 103-mer DNA oligonucleotide product (22) synthesized using a 0.1 M solution of 5-(3,5-bis(trifluoromethyl)phenyl)-1H-tetrazole (8) as activator solution, as described in Example 4.

Various terms are used herein to refer to aspects of the present invention. To aid in the clarification of the description of the components of the invention, the following descriptions are provided.

It is to be noted that the term "a" or "an" entity refers to one or more of that entity; for example, an oligonucleotide refers to one or more oligonucleotides. As such, the terms "a" or "an", "one or more" and "at least one" are used interchangeably herein and are not intended to limit the scope of the invention.

The term "oligonucleotide" as used herein refers to a single stranded chain of either deoxyribonucleotides or ribonucleotides or chemical modifications thereof, such as nucleotides with a 2'-O-4'C-methylene bridge in their sugar portion, which are the constituting nucleotides of locked nucleic acids (LNA). Modifications include, but are not limited to, those which provide other chemical groups that incorporate additional charge, polarizability, hydrogen bonding, electrostatic interaction, and functionality to the individual nucleotides or their corresponding bases or to the oligonucleotides as a whole. Such modifications include, but are not limited to, modified bases such as sugar modifications at the 2'-position of the nucleoside, pyrimidine modifications at the 5-position of the heterocyclic base, purine modifications at the 8-position of the heterocyclic base, modifications at the exocyclic amine group of cytosine bases, methylations, bases that can be part of unusual base-pairing combinations such as the isobases isocytidine and isoguanidine and the like. Modifications further include attached labels and reporter molecules, such as fluorescent dyes, biotin, minor groove binders and the like that are known to those skilled in the art. In addition modifications include modified phosphate groups of the oligonucleotides, examples being phosphorothioate oligonucleotides, methylphosphonate oligonucleotides, phosphoramidate oligonucleotides, phosphorodithioate oligonucleotides and other modifications known to those skilled in the art and reviewed by Micklefield, (2001) Current Medicinal Chemistry 8:1157-1179, which is incorporated herein by reference in its entirety. Oligonucleotides, as referred to in this invention can consist of any combinations of the nucleotides and their modifications described above and can have either a few, e.g. up to 20, or many, e.g. 20 to several hundred or more, nucleotides incorporated in its chain.

An "RNA oligonucleotide" as used herein consists either entirely or to a large part, i.e. to more than 50% of the nucleotides which constitute the oligonucleotide, of ribonucleotides or 2'-modified ribonucleotides like 2'-O-methyl-ribonucleotides, 2'-O-methoxyethyl-ribonucleotides, 2'-fluoro-ribonucleotides or the like, whereas a "DNA oligonucleotide" as used herein consists either entirely or to a large part, i.e. to more than 50% of the nucleotides which constitute the oligonucleotide, of deoxyribonucleotides.

The term "phosphoramidite" as used herein refers to a phosphorous acid diester dialkylamide as depicted in formula (9), which is comprised of a trivalent phosphorous atom bonded to one dialkylamino group (NR'R") and two alkoxy or aryloxy groups O—$R_1$ and O—$R_2$.

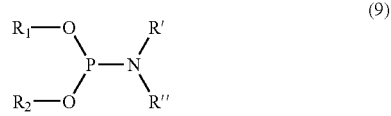

(9)

wherein $R_1$ and $R_2$, R' and R" each taken separately are selected from any of the substituents which would be known to those of skill in the art. By way of non-limiting example, $R_1$ and $R_2$, R' and R" each taken separately, may represent alkyl, aralkyl, cycloalkyl and cycloalkylalkyl. In the context of oligonucleotide synthesis phosphoramidites may either contain an alkoxy group which comprise a nucleoside or oligonucleotide moiety, or may exclusively contain non-nucleosidic alkoxy or aryloxy groups. The latter are used to introduce modifications into oligonucleotides such as terminal phosphate groups, reporter groups, haptens or other modifications known to those skilled in the art and as reviewed by Beaucage and Iyer (1993) Tetrahedron 49:1925-1963, which is incorporated herein by reference in its entirety. In the presence of a suitable catalyst phosphoramidites react with hydroxyl groups to form phosphite triesters.

"Nucleoside phosphoramidites" as used herein are phosphoramidites in which phosphorous acid is esterified to a protected nucleoside or a protected oligonucleotide (group $R_1$ of formula (9)). The second phosphorous acid ester function is comprised of a phosphate protective group (group $R_2$ of formula (9)). Nucleoside phosphoramidites carry a temporary protective group which is removed in the course of the synthesis of oligonucleotides and may contain one or more additional protective groups attached to the nucleoside portion of the molecule which are removed after the synthesis of the oligonucleotides. In order to further illustrate the term nucleoside phosphoramidite commercially marketed examples of nucleoside phosphoramidites are depicted in formulae (10) and (11). Formula (10) depicts a DNA phosphoramidite and formula (11) an RNA phosphoramidite. Formula (12) depicts a dimer phosphoramidite as an example of a nucleoside phosphoramidite derived from a protected oligonucleotide.

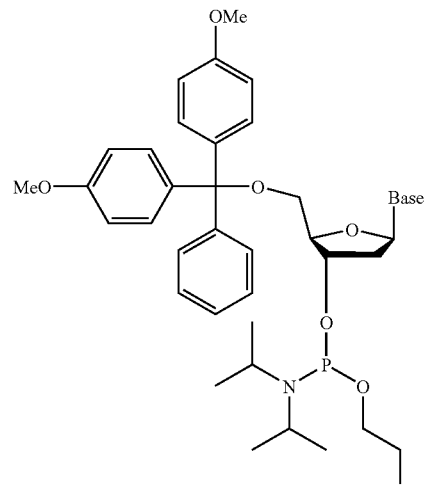

(10)

-continued

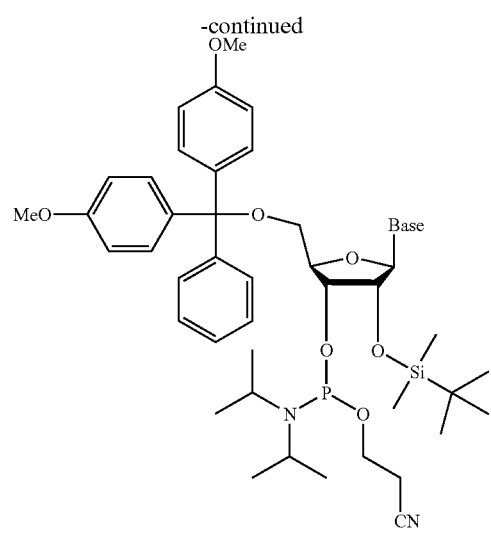

(11)

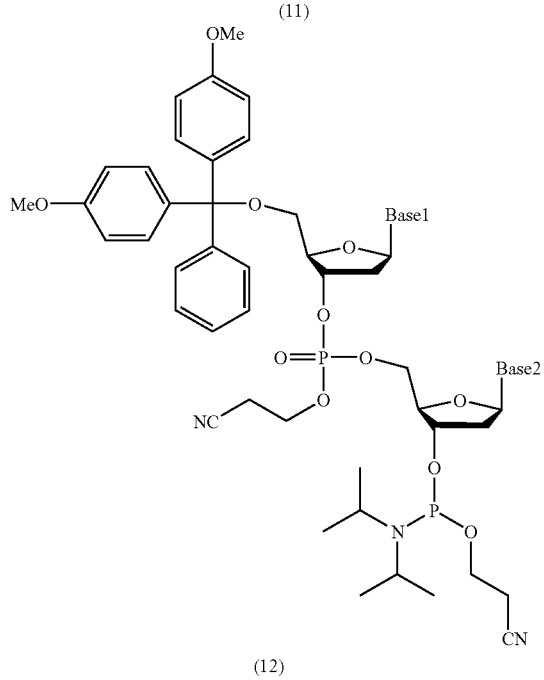

(12)

wherein Base, Base1 and Base2=protected or unprotected nucleobases.

The term nucleoside phosphoramidite is, however, not limited in any way by the nature of the examples (10) to (12). Any other nucleosides, either DNA nucleosides or RNA nucleosides or any modifications thereof, including, but not limited to 2'-modified nucleosides such as 2'-O-methylnucleosides, 2'-O-methoxyethylnucleosides and 2'-fluoronucleosides, nucleosides with bicyclic sugar moieties such as LNA nucleosides, arabino-nucleosides, nucleosides with 6-membered sugar rings such as D-altriol nucleosides as described by Allart et al. (1999) Chem Eur. J. 5:2424-2431, or anhydrohexitol nucleosides as described by Van Aerschot et al. (2001) Nucleic Acids Res. 29:4187-94, or any other modified nucleosides known to those skilled in the art could be part of nucleoside phosphoramidites as used herein. The nucleobases of such nucleosides may either be one of the main naturally occurring nucleobases, i.e. the purine bases adenine and guanine and the pyrimidine bases thymine, cytosine and uracil, or be modified nucleobases, including, but not limited to 5-methylcytosine, xanthine, hypoxanthine, 2-aminoadenine, 6-methyl and other alkyl derivatives of adenine and guanosine, 2-thiouracil, 2-thiothymine, 5-bromouracil, 7-deazaguanine, 7-deazaadenine and any other modified nucleobase known to those skilled in the art. In many instances, but not in any case the nucleobase of nucleoside phosphoramidites is protected wherein one or more functionalities of the nucleobase bears a protective group, non-limiting examples being in N6-benzoyladenine, N4-benzoylcytidine, N2-isobutyrylguanine, N2-(N,N-dimethylformamidino)guanosine, N3-anisoylthymine or O6-dichlorophenyl-N-2-isobutyrylguanine. A great variety of such protective groups for nucleobases has been disclosed in the technical literature as described e.g. by Beaucage et al. (1992) Tetrahedron 48:2223-2311. The term nucleoside phosphoramidite as used herein includes any suitable combination of protective groups and nucleobases known to those skilled in the art. The nucleobase of nucleoside phosphoramidites as used herein may, however, also be unprotected, for instance in commercially available deoxythymidine phosphoramidites, or in nucleoside phosphoramidites of other nucleobases as demonstrated by Gryaznov and Letsinger (1992) Nucleic Acids Res. 20:1879-1882, and Hayakawa et al. (1998) J. Am. Chem. Soc. 120:12395-12401, each of which is incorporated herein by reference in its entirety.

The phosphoramidites (10) to (12) carry the commonly employed bis(4-methoxyphenyl)phenylmethyl (dimethoxytrityl="DMT") group as temporary protective group. Nucleoside phosphoramidites as used herein are, however, not limited by the nature of the employed temporary protective group. Temporary protective groups for nucleoside phosphoramidites include, but are not limited to substituted triphenylmethyl groups other than the DMT-group, including but not limited to the 9-phenylxanthen-9-yl ("pixyl") group, the 9-fluorenylmethoxycarbonyl ("Fmoc") group and photolabile protective groups, e.g. the ((α-methyl-2-nitropiperonyl)-oxy)carbonyl ("MeNPOC") group as described by McGall et al. (1997) J. Am. Chem. Soc. 119:5081-5090. Temporary protective groups of nucleotide synthons are reviewed by Seliger (2000) in *Current Protocols in Nucleic Acid Chemistry*, 2.3.1-2.3.34, eds. Beaucage, S. L., Bergstrom, G. D. Glick, G. D. and Jones, R. A., J. Wiley & Sons Inc. NY, which is incorporated herein by reference in its entirety. Nucleoside phosphoramidites as used herein may carry any suitable temporary protective group known to those skilled in the art.

The RNA phosphoramidite (11) carries a tert-butyldimethylsilyl protective group at the 2'-O-position. RNA nucleoside phosphoramidites as used herein are, however, not limited by the nature of the employed 2'-O-protective group. 2'-O-protective groups for RNA nucleoside phosphoramidites as used herein include, but are not limited to the (triisopropylsilyl) oxymethyl ("TOM") group as described by Pitsch et al. (2001) Helv. Chim. Acta 84:3773-3795, the methoxytetrahydropyranyl ("MTHP") group as described by Lehmann et al. (1989) Nucleic Acids Res. 17:2379-2390, the 1-(2-fluorophenyl)-4-methoxypiperidin-4-yl ("Fpmp") group as described by Capaldi and Reese (1994) Nucleic Acids Res. 22:2209-2216, and any other 2'-O-protective group for RNA phosphoramidites known to those skilled in the art. Each of these literature references is specifically incorporated herein by reference in its entirety.

The phosphoramidites (10) to (12) are phosphorous acid diisopropylamides. Nucleoside phosphoramidites as used herein are, however, not limited by the nature of the phosphorous acid amide group. In the phosphorous acid amide group of the nucleoside phosphoramidites as used herein —N(R', R") the substituents R' and R" are independently selected from an alkyl group having from about one to about ten carbons, or taken together R' and R" together form a cyclic alkylene group having from about two to up to about twenty carbons which may or may not have additional alkyl substituents attached to it and which may contain up to 3 heteroatoms selected from N, O and S included in the cyclic alkylene group.

The phosphoramidites (10) to (12) carry 2-cyanoethyl phosphate protective groups. Nucleoside phosphoramidites as used herein are, however, not limited by the nature of the phosphate protective group. Examples of other phosphate protective groups of nucleoside phosphoramidites as used herein include, but are not limited to, methyl-, allyl-, p-nitrophenylethyl-, trichloroethyl-, o-chlorophenyl- and any other phosphate protective group known to those skilled in the art which is applicable in the context of the synthesis of oligonucleotides.

In the phosphoramidites (10) to (12) the nucleosides or oligonucleotides are esterified to phosphorous acid via the 3'-hydroxyl group ("3'-phosphoramidites"). 3'-phosphoramidites are suitable for the synthesis of oligonucleotides in the 3' to 5' direction. Nucleoside phosphoramidites as used herein are, however, not limited by the position of esterification of phosphorous acid to the nucleoside or oligonucleotide. Nucleoside phosphoramidites as used herein also include, but are not limited to nucleosides and oligonucleotides which are esterified to phosphorous acid via the 5'-hydroxyl group ("5'-phosphoramidites"), or the 2'-hydroxyl group ("2'-phosphoramidites") or, in case of hexose nucleosides or nucleosides derived from other modified sugars, any other hydroxyl group of the nucleoside. 5'-Phosphoramidites are suitable for the synthesis of oligonucleotides in 5' to 3' direction as described by Robles et al. (1995) Nucleic Acids Res. 23:4151-61, which is incorporated herein by reference in its entirety.

The term "phosphoramidite approach" as used herein refers to the synthesis of oligonucleotides with phosphoramidites. The phosphoramidite approach is characterized by condensing phosphoramidites, in particular nucleoside phosphoramidites, with nucleoside monomers or oligonucleotides which comprise a hydroxyl group in the presence of a catalyst, termed "activator", as depicted in Scheme 1. The reaction product of such a condensation is a phosphorous acid triester that is subsequently oxidized to a phosphoric acid triester. The phosphoramidite approach has been reviewed by Beaucage and Iyer. (1992) Tetrahedron 48:2223-2311.

Typically, oligonucleotide synthesis through the phosphoramidite approach involves a number of chemical reactions that are performed in a cyclical repetitive manner throughout the synthesis, each cycle adding one or more nucleotide units to the growing oligonucleotide chain. The chemical reactions which constitute a cycle include a deprotection reaction which removes a temporary protective group to liberate a functional group for further chain elongation, a coupling reaction which incorporates one or more nucleotide units into the oligonucleotide to be synthesized, and an oxidation reaction which transforms the phosphite triester coupling product to a phosphate triester. Optionally, a capping reaction that blocks those functional groups which were not elongated in the coupling reaction is inserted in the cycle.

The extension of the oligonucleotide chain in the course of an oligonucleotide synthesis via the phosphoramidite approach is typically performed in the 3' to 5' direction by coupling 3'-phosphoramidites carrying suitable protective groups at the 5'-position, e.g. the widely employed DMT-group, to form a linkage to the 5'-position of the growing chain. The extension of the oligonucleotide chain may alternatively be pursued in the 5' to 3' direction by adding 5'-phosphoramidites in the coupling reaction carrying suitable protective groups at the 3'-position, e.g. a DMT-group, to form a linkage to the 3'-position of the growing chain.

Phosphoramidites used in the coupling step of an oligonucleotide synthesis cycle typically are mononucleotide synthons, as exemplified in formulae (10) and (11), but also include oligonucleotide synthons, e.g. dinucleotide synthons, as described by Kumar and Poonian (1984) J. Org. Chem. 49:4905-12, which is incorporated herein by reference in its entirety, trinucleotide synthons, as described by Ono et al. (1995) Nucleic Acids Res. 23:4677-82, which is incorporated herein by reference in its entirety, or synthons that consist of more than 3 nucleotide units.

The phosphoramidite approach also includes the modification of oligonucleotides with non-nucleosidic phosphoramidites. Coupling of non-nucleosidic phosphoramidites to protected oligonucleotides which comprise a hydroxyl group provides a convenient way to manipulate and fine-tune the properties of the synthetic oligonucleotide to the demands of the particular application of the oligonucleotide. Examples include, but are not limited to the introduction of reporter groups to allow the facile detection of the modified oligonucleotides, e.g. fluorescent dyes, the introduction of haptens to facilitate the specific capture and detection of oligonucleotides and their reaction products in diagnostic assays, e.g. biotin or digoxigenin, the introduction of lipophilic modifiers to enhance the uptake of oligonucleotides in cells, e.g. cholesterin, the introduction of modifiers to increase the biocompatibility and to reduce the exonucleolytic degradation of oligonucleotides, e.g. polyethylene or other groups which block the terminal hydroxyl groups, the introduction of affinity modifiers to increase the affinity of oligonucleotides to complementary sequences, e.g. intercalators or nucleic acid groove binders, and the conjugation of peptides to achieve a variety of specific effects including targeted delivery to specific cell lines in an organism.

The term "coupling reaction" as used herein refers to the chemical reaction of a phosphoramidite with a protected nucleoside or oligonucleotide which comprise a hydroxyl group in the presence of a catalyst. The reaction product is a phosphite triester. Coupling reactions may be performed under cooling, e.g. at temperatures ranging from about −30° C. to about +20° C., with heating, e.g. at temperatures ranging from about +20° C. to about +80° C., or, most conveniently without external cooling or heating at ambient temperature. In a preferred embodiment of the present invention, coupling reactions are performed at about ambient temperature. Coupling reactions are typically performed in acetonitrile as solvent, but other solvents, including but not limited to dichloromethane, tetrahydrofuran, succinic acid dinitrile and adipic acid dinitrile or mixtures of such solvents with each other or with acetonitrile can also be employed. In a preferred embodiment of the present invention coupling reactions are performed in acetonitrile or in mixtures of acetonitrile with other solvents. Coupling reactions can either be performed with all reaction partners including the catalyst being completely dissolved in the solvent of the reaction or with one or two of the reaction partners and catalyst being only partially dissolved or completely undissolved as in, e.g., polymer supported reactions. Coupling reactions as used herein can have reaction times ranging from seconds to days, depending on the reactivity of the reactants and the efficiency of the employed catalyst. In a preferred embodiment of the present invention the reaction time of coupling reactions ranges from about one second to about fifteen minutes.

"Coupling time" as used herein is the reaction time of a coupling reaction.

The term "aryl-substituted 5-phenyl-1H-tetrazole" as used herein refers to a compound of formula (13).

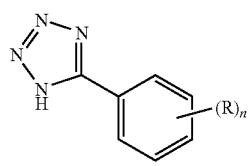

(13)

In said compounds the phenyl ring of 5-phenyl-1H-tetrazole carries one or more R substituents, wherein R is independently selected from the group including but not limited to alkyl, alkenyl, alkynyl, aryl, alkoxy, aryloxy, halogeno, nitro, cyano, amino, alkylamino, isocyanato, carboxalkyl, carboxaryl, perfluoroalkyl or other substituted alkyl, substituted aryl or any other common substituent in organic chemistry known to a skilled artisan and n is an integer selected from 1-5. Any substituent at the phenyl ring may independently occupy any position relative to the tetrazole moiety at the phenyl ring. For example, in case a single substituent is present the substituent may be attached in ortho-, meta- or para-position relative to the tetrazole moiety. As another example, in case two substituents are present and one substituent is attached at the meta-position relative to the tetrazole moiety, the other substituent may be attached at any remaining position of the phenyl ring.

The term "perfluoroalkyl substituent" as used herein refers to a substituent that is derived from an alkyl group by substituting at least two hydrogen atoms of the alkyl group by fluorine atoms. Examples of perfluoroalkyl substituents as used herein include, but are not limited to the substituents trifluoromethyl, difluoromethyl, pentafluoroethyl, 2,2,2-trifluoroethyl, heptafluoro-n-propyl, and 2,2,2,2',2',2'-hexafluoroisopropyl.

The term "solid phase oligonucleotide synthesis" (SPOS) as used herein refers to the synthesis of oligonucleotides on a solid support. Advantages of SPOS are that the work-up of all reactions can be performed conveniently by filtration steps and that the method is easily automated. SPOS is described by Gait, ed. (1984) in *Oligonucleotide Synthesis: A Practical Approach*, IRL Press, Oxford, UK and Eckstein, ed., (1991) in *Oligonucleotides and Analogs: A Practical Approach*, IRL Press, Oxford, UK, each of which is incorporated herein by reference in its entirety. SPOS via the phosphoramidite approach involves the cyclical repetition of deblocking a support bound protected nucleoside or oligonucleotide, coupling a nucleoside phosphoramidite with the deblocked support-bound nucleoside or oligonucleotide and oxidizing the resulting support bound phosphite triester to a phosphate triester. A capping step is commonly added to this cycle either before or after the oxidation reaction in order to prevent uncoupled support bound oligomers from further growth in subsequent reaction cycles.

The term "nucleophilic catalyst" as used herein refers to a compound C that catalyses the reaction of an electrophile E in an electrophilic compound E-A, wherein A is a leaving group, with a nucleophile Nu in a nucleophilic compound Nu-H, wherein H is hydrogen, by forming an intermediate E-C with the electrophile which reacts much faster with the nucleophilic compound Nu-H than the electrophilic compound E-A. Particular examples of nucleophilic catalysts include, but are not limited to N-methylimidazole, 4-(N,N-dimethylamino)pyridine and 4-pyrrolidinopyridine. Examples of reactions which are catalyzed by nucleophilic catalysts include acylations of hydroxy functions with carboxylic acid anhydrides, e.g. the acetylation of a nucleoside comprising a hydroxyl group with acetic anhydride, tritylation reactions, e.g. the dimethoxytritylation of nucleoside hydroxy groups, silylation reactions, e.g. the silylation of hydroxy functions with silyl chlorides, and other reactions of electrophilic compounds with nucleophilic compounds as described for instance in Scriven (1983) Chem. Soc. Rev. 12:129-161, which is incorporated herein by reference in its entirety.

The term "phosphitylating agent" as used herein refers to a phosphorous acid bis(dialkylamide) monoester as depicted in formula (6), which is comprised of a trivalent phosphorous atom bonded to two dialkylamino groups (NR'R") and one alkoxy group O—R

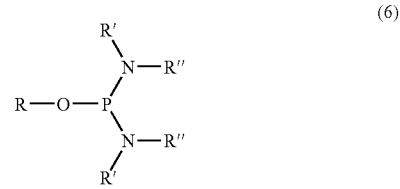

(6)

wherein R is phosphate protective group, e.g. β-cyanoethyl; and R' and R" are independently selected from an alkyl group having from about one to about ten carbons, or taken together R' and R" together form a cyclic alkylene group having from two to up to twenty carbons which may or may not have additional alkyl substituents attached to it and which may contain up to 3 heteroatoms selected from N, O and S included in the cyclic alkylene group.

Phosphitylating agents as used herein are employed in the preparation of phosphoramidites, in particular nucleoside phosphoramidites, as depicted in Scheme 2 above. In this method a compound with a hydroxyl group, e.g. a nucleoside or oligonucleotide which comprises a hydroxyl group, is reacted with a phosphitylating agent of formula (6) in the presence of a catalyst to generate a phosphoramidite. Phosphitylating agents of formula (6) are widely used for the preparation of nucleoside phosphoramidites comprising a phosphorous acid ester function which constitutes a phosphate protective group (group R of formula (6)). Examples of such phosphate protective groups include, but are not limited to 2-cyanoethyl-, methyl-, allyl-, p-nitrophenylethyl-, trichloroethyl-, o-chlorophenyl- and any other phosphate protective group known to those skilled in the art. In one embodiment of the present invention, the phosphitylating agent is useful to prepare nucleoside phosphoramidites and the respective phosphate protective group is a 2-cyanoethyl-group. In a preferred embodiment, the phosphitylating agent is bis(diisopropylamino)-2-cyanoethoxyphosphane (14) which can be employed to prepare a variety of nucleoside phosphoramidites (15), including, but not limited to DNA nucleoside phosphoramidites (10) and RNA nucleoside phosphoramidites (11).

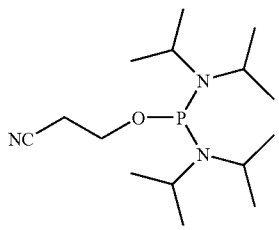

(14)

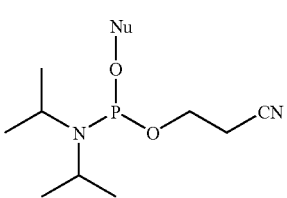

(15)

wherein Nu is selected from the group including, but not limited to a monomeric or oligomeric nucleoside/nucleotide group.

The present invention discloses novel methods for the synthesis of oligonucleotides via the phosphoramidite approach and for the synthesis of phosphoramidites. The methods are based on the application of novel aryl substituted 5-phenyl-1H-tetrazoles as catalysts in coupling reactions of the phosphoramidite approach for the synthesis of oligonucleotides and in the synthesis of phosphoramidites with phosphitylating agents.

In one embodiment, the present invention discloses efficient activators for the synthesis of oligonucleotides via the phosphoramidite approach as depicted in Scheme 1 above. The activators of the invention are aryl substituted 5-phenyl-1H-tetrazoles of formula (13) wherein at least one of the R substituents is comprised of a perfluoroalkyl group. Aryl substituted 5-phenyl-1H-tetrazoles with electronegative substituents on the aromatic ring, in particular 5-(4-nitrophenyl)-1H-tetrazole (7), are efficient activators for the synthesis of DNA and RNA oligonucleotides as described e.g. by Froehler and Matteucci (1983) Tetrahedron Letters 24:3171-3174, Pon (1987) Tetrahedron Letters 28:3643-3646, and Tanaka et al. (1986) Nucleic Acids Res. 14:6265-6279. The activity of such aryl substituted 5-phenyl-1H-tetrazoles appears to be related to their pKa-value with lower pKa-values being associated with better coupling promotion. For example, the pKa-value of (7) is 3.7, which is more than one order of magnitude lower than the pKa-values of 1H-tetrazole (pKa 4.8) and 5-phenyl-1H-tetrazole (pKa 4.8). However, substituted 5-phenyl-1H-tetrazoles generally have low solubilities in the solvents that are commonly employed in coupling reactions of phosphoramidites which limits their practical usefulness. For instance, the maximum concentration of (7) in the most commonly employed solvent for coupling reactions, acetonitrile, is 0.12 M at 25° C., and the maximum concentration of 5-phenyl-1H-tetrazole in acetonitrile is 0.08 M. Commercial activator solutions in acetonitrile contain activators at concentrations well above these concentrations, e.g. 1H-tetrazole is employed as a 0.45 M solution, and DCI, ETT and BTT are employed as 0.25 M solutions, respectively. The solubility of activators for the synthesis of oligonucleotides in acetonitrile should generally be much higher than the solubility of (7) and should at least allow the preparation of stable solutions with a concentration greater than 0.25 M at 25° C., preferably even greater than 0.5 M at 25° C.

Another problem with aryl substituted 5-phenyl-1H-tetrazoles of relatively low solubility is that they have a high tendency to crystallize if used as concentrated solutions in acetonitrile, which impacts the stability of such solutions. If such activators are applied at concentrations near saturation then even slight drops in the temperature during oligonucleotide synthesis may result in the deposition of crystalline material in the activator reservoir of a DNA/RNA synthesizer thus lowering the effective concentration of the activator. More importantly, such deposition may also occur in the valves, the lines or the reactor of the synthesizer causing synthesis interruption and machine failure. Crystallization may also occur during shipping or storage of an activator solution thus requiring the solution to be treated by heating and/or agitation to redissolve the deposited material. Such additional handling is time consuming and costly in the routine preparation of oligonucleotides. The present invention relates to activators derived from 5-phenyl-1H-tetrazoles by introducing at least one perfluoroalkyl substituent on the phenyl ring. Such activators are highly soluble in the common solvents of phosphoramidite coupling reactions, particularly in acetonitrile. They are also highly efficient activators and can therefore be employed in the synthesis of oligonucleotides at concentrations well below their maximum concentration, thus avoiding any problems associated with the use of activator solutions at concentrations near saturation.

Perfluoroalkyl substituents are known to be electronegative substituents as demonstrated, for example, by the Hammett constants of the trifluoromethyl substituent $\sigma_p$ (0.53) and $\sigma_m$ (0.46) as described in March (1985) Advanced Organic Chemistry 3$^{rd}$ Ed., John Wiley & Sons, pp. 242-250, and therefore lead to lower pKa-values of the respective tetrazole derivatives. The relatively low pKa-values of the activators may, without wishing to be bound to a particular theory, be responsible for their high activity.

Generally, a useful activator for the synthesis of oligonucleotides should fulfil a range of criteria which can be summarized as follows:

A. High solubility in acetonitrile (preferred max. concentration at 25° C.$\geq$0.5 M);

B. High activity, i.e. high coupling efficiency (preferably $\geq$99% per coupling) in the synthesis of DNA-oligonucleotides;

C. High activity, i.e. high coupling efficiency (preferably $\geq$98% per coupling) in the synthesis of RNA-oligonucleotides;

D. Low levels of side reactions in the synthesis of oligonucleotides;

E. Safe handling, i.e. the respective compound should not be hazardous, in particular, it should not be explosive;

F. Low hygroscopy; and

G. Availability from commercial sources or through simple and efficient synthesis. Activators of the present invention fulfil all of the above criteria as demonstrated by way of example with the novel activator 5-(3,5-bis(trifluoromethyl)phenyl)-1H-tetrazole (8) as discussed below.

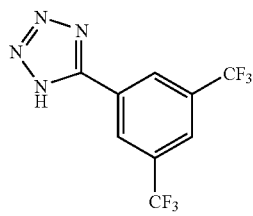

(8)

A. The maximum concentration of (8) is 0.94 M in acetonitrile at 25° C. as demonstrated in Example 1. The solubility of (8) is much higher than the desired concentration in acetonitrile, whereas the non-substituted 5-phenyl-1H-tetrazole has a rather poor solubility in acetonitrile of 0.08 M. This example demonstrates the pronounced effect of the introduction of perfluoroalkyl substituents on the solubility of the respective activator. The commercial activators ETT and BTT have solubilities of 1.52 M and 0.44 M, respectively, which is deemed very satisfactory in the case of ETT, but only moderately sufficient in the case of BTT, because concentrations of 0.5 M in acetonitrile are not available for this activator and care must be exercised if moderately concentrated solutions are employed in order to avoid crystallization and or precipitation.

It is worth mentioning that, as demonstrated in further examples below, (8) is an efficient activator at concentrations substantially below its maximum solubility, e.g. when used as 0.1 M or 0.25 M solution in acetonitrile. Such solutions can be employed without any risk of undesired crystallization. Solutions of (8) in acetonitrile can also be mixed with deblock or capping solutions in any ratio without concomitant precipitation of solid materials as demonstrated in Example 2 for an 0.5 M solution of (8). In contrast, mixing of an 0.5 M solution of DCI in acetonitrile with deblock solution (3% trichloroacetic acid in dichloromethane) in ratios of 1/1, v/v, or 1/9, v/v, resulted in the immediate formation of precipitates.

Figure 1B:
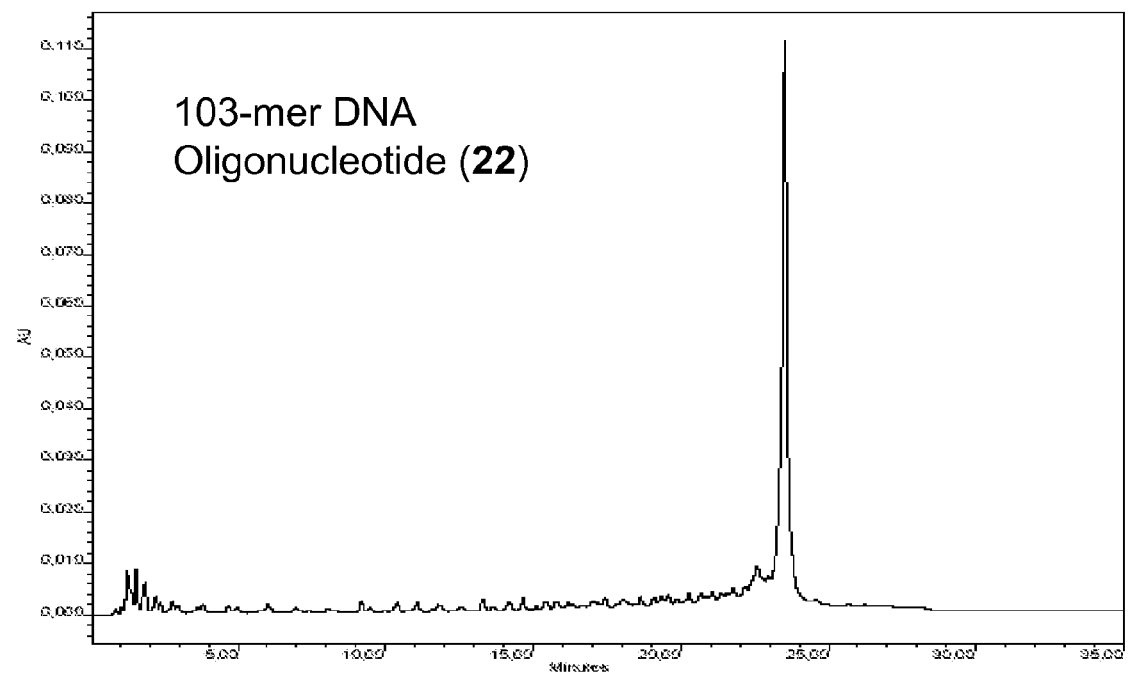

B. Activator (8) promotes the efficient synthesis of DNA oligonucleotides as demonstrated in Examples 3 to 7. In Example 3, a 0.1 M solution of (8) was employed to synthesize the homo-oligonucleotide $dT_{10}$ (16) (SEQ ID NO:13), which was obtained in 97.2% purity as measured by anion exchange HPLC. In Example 4, a 0.1 M solution of (8) was employed to synthesize the 22-mer to 103-mer heterosequence DNA oligonucleotides (17) to (22), which were obtained in excellent yields and purities as demonstrated in Table 1 and FIG. 1. In Example 5, a measurement of the coupling efficiency in the synthesis of oligonucleotide (17) through a spectrophotometric DMT assay demonstrated that coupling efficiencies above 99.0% were obtained.

TABLE 1

Yield and Purity of Oligonucleotides (17) to (22).

| | Sequence | Quantity by UV- (OD) | Purity by AX-HPLC (%) | MALDI-TOF mass (m/z) calc. | observ. |
|---|---|---|---|---|---|
| (17) | 5'-d(CGC-TCA-TCT-TCA-AGT-CCA-CCC-T)-3', (SEQ ID NO: 1) 22-mer | 133 | 69.1 | 6566 | 6566 |
| (18) | 5'-d(AGG-GTG-GAC-TTG-AAG-ATG-AGC-G)-3', (SEQ ID NO: 2) 22-mer | 143 | 65.4 | 6904 | 6905 |
| (19) | 5'-d(GCT-CAA-CAC-AAA-GAT-GTC-TTC--TCT-GTG)-3', (SEQ ID NO: 3) 27-mer | 128 | 62.5 | 8234 | 8235 |
| (20) | 5'-d(CAG-TGC-AGC-TCC-TAG-CAG-CCT--AGC-GTA-CTA-GTC-TT)-3', (SEQ ID NO: 4) 35-mer | 210 | 68.3 | 10683 | 10687 |
| (21) | 5'-d(CAG-TCC-TAG-TCA-CAG-TCC-AGT--CGC-TCA-AGC-GTC-CAG-TTG-CAC-AGG--TCA-CCT)-3', (SEQ ID NO: 5) 51-mer | 171 | 77.4 | 15556 | 15567 |
| (22) | 5'-d(GCC-AGC-CAT-GAA-GGA-GGA-GGA-CGG--CCG-CCT-GCT-GGC-CAG-CAA-GTG-CGT-GAC--CGA-CGA-GTG-CTT-CTT-CTT-CGA-GCG-CCT--GGA-GAG-AAC-AAC-TAC-AAC-TAC-TAC-T)-3', (SEQ ID NO: 7) 103-mer | 201 | 65.4 | 31820 | n.a. |

The very high activation efficiency of (8) is further demonstrated in Examples 6 and 7 wherein very short coupling times were employed in the synthesis of DNA heterosequence oligonucleotides. For example, the crude oligonucleotide 22-mer (17) was obtained employing a coupling time of 10 sec. per coupling in 59% purity by anion exchange HPLC (non-desalted), and the crude oligonucleotide 51-mer (21) was obtained employing a coupling time of 15 sec. per coupling in 46% purity by anion exchange HPLC (non-desalted).

Figure 2:
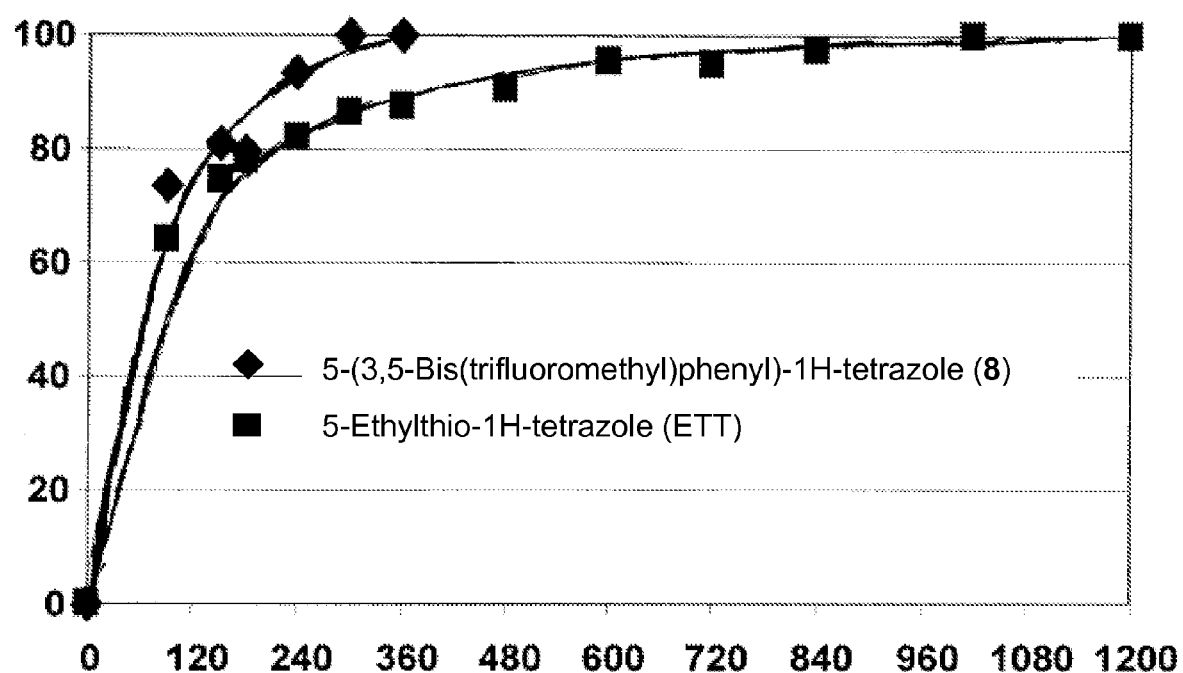
FIG. 2 depicts the time course of the coupling reaction of DMT-rA(tac)-amidite (23) with dT-si (24) in the presence of either 5-(3,5-bis(trifluoromethyl)phenyl)-1H-tetrazole (8) or ETT as activators, as described in Example 8.

C. Activator (8) promotes the efficient coupling of 2'-O-tert-butyldimethylsilyl RNA phosphoramidites (11) as demonstrated in Examples 8 to 11. In Example 8, DMT-rA(tac)-amidite (23) was coupled with the 5'-OH nucleoside dT-si (24) as depicted in Scheme 3 in the presence of (8) in an NMR tube. The formation of the phosphite triester product (25) was monitored by P-NMR. The conversion rate of the amidite (23) to product (25) was greater than 80% after 2.5 minutes and the reaction was essentially complete after 5 minutes. Repeating the experiment with ETT as activator under otherwise identical conditions resulted in a conversion rate greater than 80% after 4 minutes and in a complete reaction after 17 minutes. A graphical representation of the observed reaction kinetics is displayed in FIG. 2. This example demonstrates the superior performance of the activators of the invention compared to commercial activators.

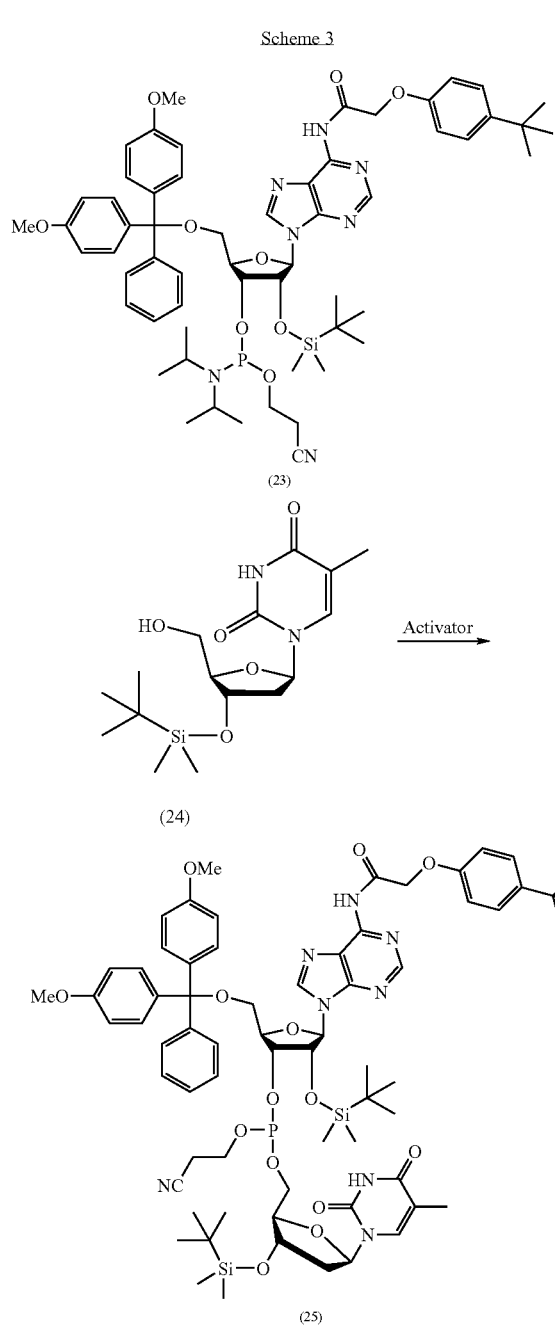

Scheme 3

(23)

(24)

(25)

In Example 9 rC(tac)-amidite (26) was coupled with the support-bound oligonucleotide dT$_6$ in the presence of (8). A 0.1 M solution of (8) was applied as activator solution and the coupling time was varied from 2 minutes to 10 minutes. The coupling efficiency of the amidite (26) was determined from the HPLC-chromatogram of the synthesized mixture of oligonucleotides dT$_6$ and 5'-rCdT$_6$-3' as described in Example 9. The coupling efficiency was close to 80% after 2 minutes coupling time and the reaction was essentially complete after 6 minutes coupling time.

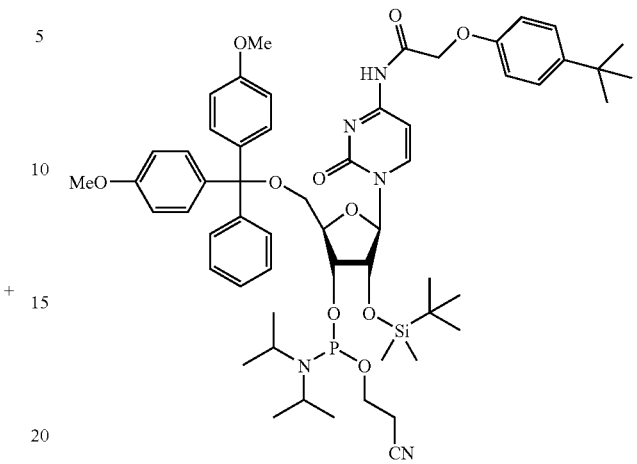

(26)

Figure 3A:
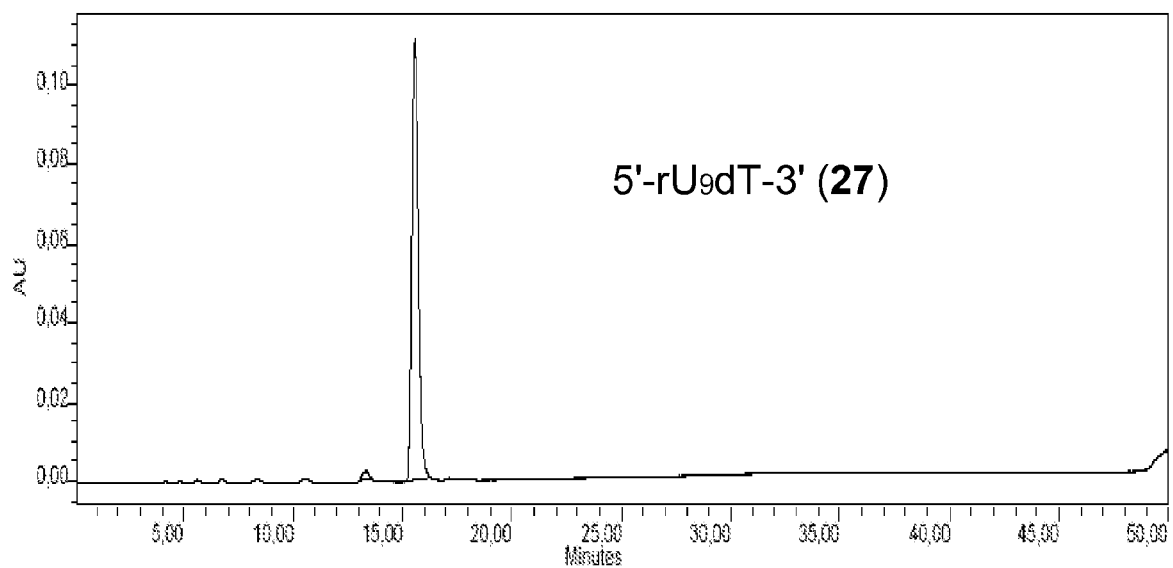
FIGS. 3A and 3B display the reversed phase HPLC chromatogram of the RNA oligonucleotide products (27) and (28) synthesized using a 0.1 M solution of 5-(3,5-bis(trifluoromethyl)phenyl)-1H-tetrazole (8) as activator solution, as described in Examples 10 and 11.
Figure 3B:
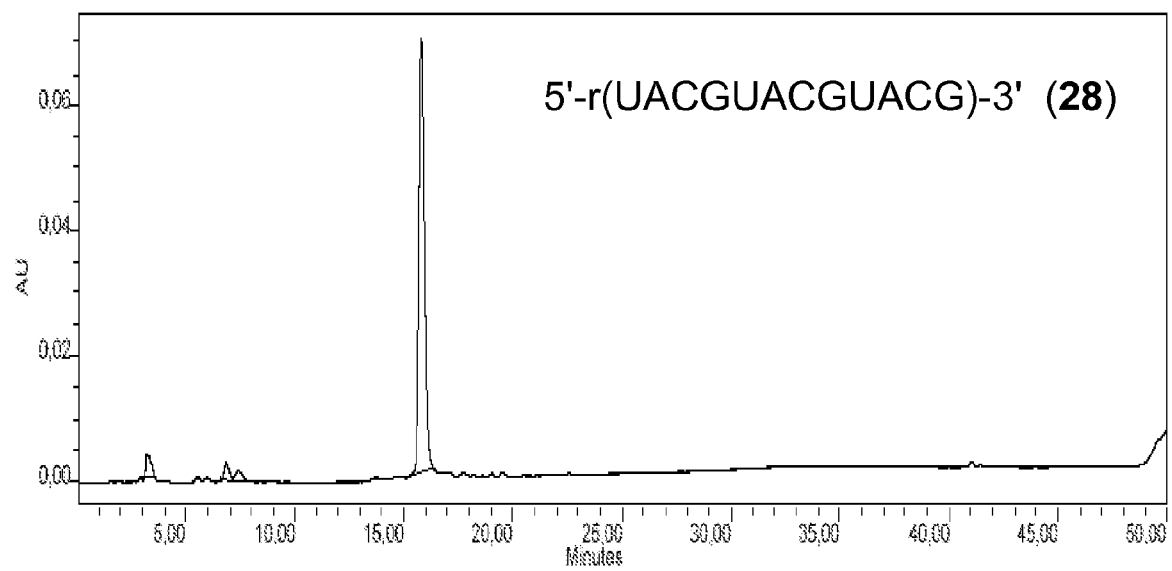

In Examples 10 and 11 the RNA oligonucleotides 5'-rU$_9$dT-3' (27) (SEQ ID NO:8) and 5'-r(UAC-GUA-CGU-ACG)-3' (28) (SEQ ID NO:9) were synthesized on CPG solid supports. A 0.1 M solution of (8) was employed as activator solution and the oligonucleotides were obtained in 98% and 89% purity, respectively, as measured by reversed phase HPLC. The respective HPLC chromatograms are depicted in FIG. 3. These examples demonstrate the high efficiency of the activators of the invention in the synthesis of RNA oligonucleotides on solid supports and the very high coupling efficiencies that are obtainable with such activators.

In Example 12, a 0.1 M solution of (8) was employed as activator solution in the synthesis of the 2'-O-methyl RNA oligonucleotides 5'-r(GUG-UGU-GUG-UGU-GUG-UGU-GU)-3' (29) (SEQ ID NO:10) and 5'-r(CGC-UCA-UCU-UCA-AGU-CCA-CCC-U)-3' (30) (SEQ ID NO:12) wherein all nucleosides are 2'-O-methyl-nucleosides. The oligonucleotides were obtained in 58% and 61% purity, respectively as measured by anion-exchange HPLC. This example demonstrates the high efficiency of the activators of the invention in the synthesis of modified RNA oligonucleotides on solid supports and the very high coupling efficiencies that are obtainable with such activators.

0.1 M solutions of (8) were employed as activator solutions in the examples for RNA syntheses which are summarized above and described in detail below. The coupling time for RNA phosphoramidites can be reduced if higher concentrations of (8), e.g. 0.25 M solutions or 0.5 M solutions, are employed.

D. Activator (8) does not cause significant levels of side reactions as demonstrated by the high purities of the oligonucleotides prepared in Examples 3 to 7 and Examples 10 to 12. However, since (8) is more acidic than other commercial activators (pKa 3.4 as demonstrated in Example 2) the occurrence of detritylation side reactions in couplings is worth consideration. Detritylation during coupling would lead to the incorporation of additional nucleotides in the growing oligonucleotide chain during the synthesis and therefore result in oligonucleotide by-products of higher length than the length of the intended product, usually sequences with one or two additional nucleotides (n+-mers). The products of any detritylation during coupling reactions are amidites and/or support bound oligomers with free 5'-OH functions, which are likely to react with the excess of amidite that is employed.

Detritylated amidites would yield dimeric amidites from this reaction which would potentially incorporate two nucleotides in the growing chain simultaneously. Detritylated support bound oligomers would lead to the incorporation of additional nucleotides in a direct manner. This potential side reaction was investigated as described in Example 13. The DNA model oligonucleotides $dT_{10}$ (16) (SEQ ID NO:13), $dA_{10}$ (32) (SEQ ID NO:14), $dC_{10}$ (33) (SEQ ID NO:6) and 5'-d$(GT)_5$ (34) (SEQ ID NO:11) were prepared on CPG supports with an 0.1 M solution of (8) as activator solution under conditions which are expected to promote side reactions, i.e. with prolonged coupling times of 12 minutes. The same oligonucleotides were also prepared with coupling times of 90 seconds under otherwise identical conditions for comparison. The oligonucleotides were obtained in excellent yields and purities in all of these syntheses with little, if any, detectable n+-mers as measured by anion-exchange HPLC. Detritylation side reactions that occur during the coupling steps in these model synthesis are expected to proceed primarily during the coupling of the G-phosphoramidite, because tritylated guanosine residues detritylate faster than other tritylated nucleoside residues derived from natural nucleobases, as described by Treiber and Williamson (1995) Nucleic Acids Res. 23:3603-3604, which is incorporated herein by reference in its entirety. However, the observed level of the n+1-mer impurity in the sequence 5'-d$(GT)_5$-3' (34) was not greater than 0.3% even at prolonged coupling times of 12 minutes per coupling. Low levels of the n+1-mer impurity were also observed for the sequences $dT_{10}$ (16), $dA_{10}$ (32) and $dC_{10}$ (33). In conclusion, under the described conditions detritylation side reactions did not exceed 0.1% per coupling even at 12 minutes coupling time. This example demonstrates that the activators of the invention, although being more acidic than commercial activators, are applicable in SPOS without significant levels of detritylation during couplings and do not lead to the accumulation of n+-mer sequences.

E. Activator (8) has been tested under standardized conditions for explosion hazards associated with this compound. The tests were conducted according to method A.14 ("Explosion hazards") of the European Commission directive 92/69/EEC of 31 Jul. 1992 related to the classification, packaging and labelling of dangerous substances in a certified GLP laboratory by the German BAM (Bundesanstalt für Materialprüfung). The following tests were conducted:

1. Test of thermal sensitivity (heating in a steel tube with a defined orifice, "Stahlhuülsentest");
2. Test of mechanical sensitivity with respect to shock (exposure to shock from a specified mass dropped from a specified height, "Fallhammertest"); and
3. Test of mechanical sensitivity with respect to friction (subjection to friction between standard surfaces under specified conditions of load and relative motion).

The tests indicated that activator (8) is neither thermally nor mechanically sensitive, i.e. has no explosive properties and can be handled safely without the need to conduct special safety precautions for explosives during shipping, storage, handling and disposal.

F. As a solid, activator (8) is not hygroscopic as demonstrated in Example 14. In this example a 50 g sample of compound (8) was exposed to an atmosphere having 75% relative humidity for 8 days. The sample did not gain weight within the limit of accuracy of the weight measurement. Compound (8) therefore does not need special protection against moisture during storage.

G. Activators of the present invention can be prepared conveniently in one step from the respective benzonitriles through their reaction with azides as depicted in Scheme 4. Briefly, benzonitrile (35) is treated with sodium azide in a suitable solvent in the presence of a proton or Lewis acid catalyst. Examples for the synthesis of aryl-substituted 5-phenyl-1H-tetrazoles are described by Finnegan et al. (1958) J. Am. Chem. Soc. 80:3908-3911, wherein the reaction is conducted in N,N-dimethylformamide as solvent and wherein the catalyst is ammonium chloride, and by Demko and Sharpless (2001) J. Org. Chem. 66:7945-50, wherein the reaction is conducted in water as a solvent and wherein the catalyst is a zinc salt. Each of these literature references is specifically incorporated herein by reference in its entirety. In this reaction, the reaction time and temperature to achieve a nearly complete conversion of the respective benzonitrile is greatly dependent on the nature of the substituents on the aromatic ring of the benzonitrile. In general, benzonitriles with electron withdrawing substituents react under milder conditions than benzonitriles without such substituents and the required reaction temperature corresponds to the electron withdrawing strength of the substituents.

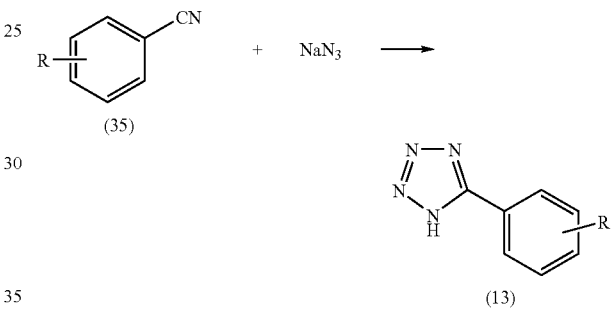

Scheme 4

Figure 4:
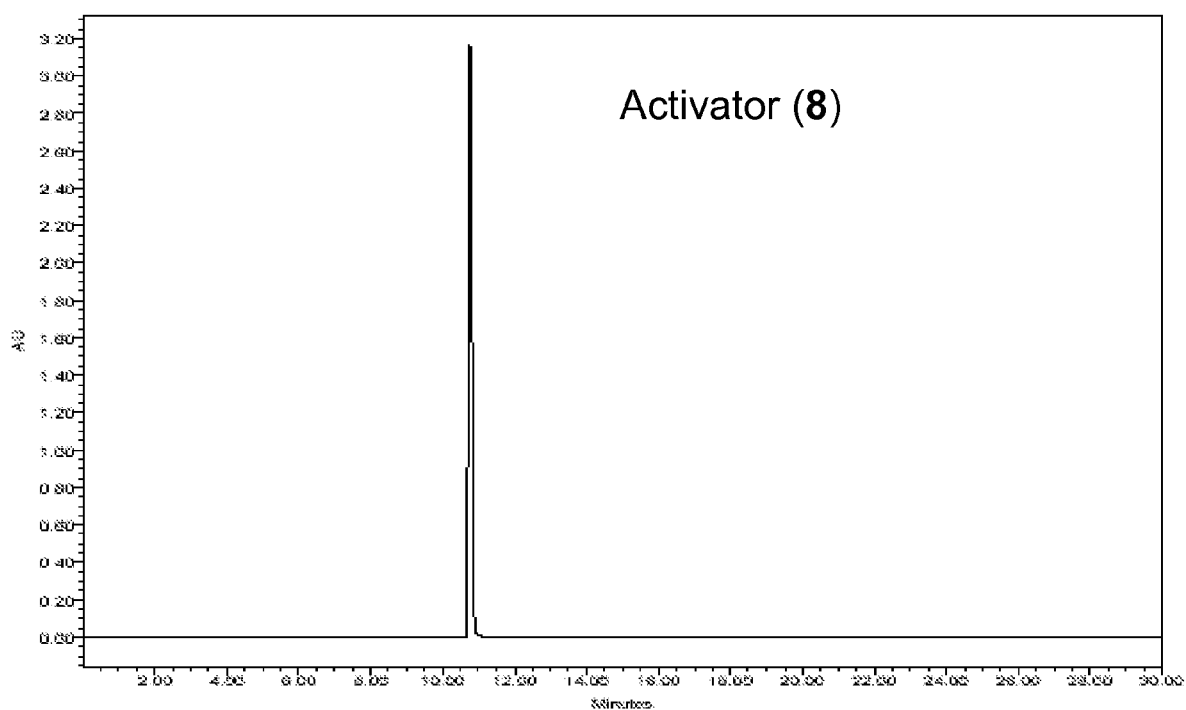
FIG. 4 depicts the reversed phase HPLC chromatogram of 5-(3,5-bis(trifluoromethyl)phenyl)-1H-tetrazole (8) synthesized in Example 15.

Activators of the present invention carry electron withdrawing perfluoroalkyl substituents on the aromatic ring and therefore react under relatively mild conditions as demonstrated in Example 15 for activator (8) wherein the synthesis is conducted at ambient temperature. In this example, the product (8) was obtained in excellent yield and purity, as depicted in FIG. 4. The synthesis as described in Example 15 is conducted under much milder conditions than other synthesis of aryl-substituted 5-phenyl-1H-tetrazoles described in the literature, which are conducted at elevated temperatures, preferably in refluxing water or in N,N-dimethylformamide at temperatures above 100° C.

In another embodiment of the present invention, the novel activators can also be applied to the synthesis of oligonucleotides in the presence of nucleophilic catalysts. Nucleophilic catalysts accelerate reactions of electrophilic reagents with nucleophiles, e.g. the catalysis of the reaction of carboxylic acid anhydrides with hydroxyl compounds by 4-(N,N-dimethylamino)pyridine. Coupling reactions of phosphoramidites with hydroxyl compounds in the presence of tetrazole derivatives are deemed to proceed via an electrophilic intermediate, i.e. a tetrazolylphosphite species, as described by Berner et al. (1989) Nucleic Acids Res. 17:853-864, and Dahl et al. (1987) Nucleic Acids Res. 15:1729-1743. The reaction of the electrophilic intermediate with a hydroxyl compound is prone to nucleophilic catalysis. This approach has been demonstrated by Pon (1987) Tetrahedron Letters 28:3643-3646 for couplings of 2'-O-tert-butyldimethylsilyl protected RNA phosphoramidites in the presence of 5-(4-nitrophenyl)-1H-tetrazole (7) wherein 4-(N,N-dimethylamino)pyridine was employed as nucleophilic catalyst. The feasibility of this approach for couplings in the presence of activators of the present invention is demonstrated in Example 16.

In Example 16, the DNA oligonucleotides $dT_{10}$ (16), $dA_{10}$ (32), $dC_{10}$ (33) and 5'-d(GT)$_5$ (34) were synthesized on CPG supports with an activator solution which contained compound (8) (0.1 M) and the nucleophilic catalyst N-methylimidazole (0.01 M). The crude oligonucleotide products were of exceptional purity. This example demonstrates that activators of the present invention can be applied advantageously in the presence of a nucleophilic catalyst.

As demonstrated by example the activators of the present invention fulfil all general criteria of activators for the synthesis of oligonucleotides. They do not have the limitations associated with some of the activators of the prior art like poor solubility, hygroscopy, insufficient activation of 2'-O-tert-butyldimethylsilyl RNA-amidites, explosive properties, etc. and give premium results with respect to product quantity and purity in the synthesis of oligonucleotides.

In another embodiment, the present invention discloses efficient activators for the preparation of phosphoramidites from compounds with hydroxy groups and phosphitylating agents as depicted in Scheme 2. The activators of the invention are aryl substituted 5-phenyl-1H-tetrazoles, as described above, wherein at least one of the R substituents is comprised of a perfluoroalkyl group. In the methods of the invention a compound with a hydroxy group is reacted with a phosphitylating agent of structure (6) to give a phosphoramidite of structure (9). In a preferred embodiment the resulting phosphoramidite is a nucleoside phosphoramidite. In a particular preferred embodiment the phosphoramidite is a nucleoside phosphoramidite and the phosphitylating agent is bis(diisopropylamino)-2-cyanoethoxyphosphane (14). Reacting nucleosides comprising a free hydroxyl group with phosphitylating agent (14) in the presence of an activator of the invention in a suitable solvent, including, but not limited to dichloromethane, THF or ethyl acetate, under conditions of time and temperature effective to yield said nucleoside phosphoramidite results in 2-cyanoethyl-diisopropylamino phosphoramidites of structure (15), which are widely used in the synthesis of oligonucleotides and which are commercially available.

In particular, phosphoramidites of structure (10) or (11) can be obtained, which represent the most widely used DNA- and RNA-phosphoramidites for the synthesis of oligonucleotides. Typically said reactions are conducted at ambient temperature, the reaction time is in the order of 10 min. to 2 hours and the solvent of the reaction is chosen in a way that it completely dissolves both the nucleoside starting material and the phosphoramidite product. The reaction can also conveniently be monitored by standard analytical methods like analytical HPLC and thin layer chromatography (TLC) to determine its endpoint. The methods of the invention lead to very pure nucleoside phosphoramidites within short reaction times as demonstrated in the synthesis of DMT-dG(ib)-amidite (36) in Example 17, wherein the solvent of the reaction is dichloromethane, the reaction temperature is ambient temperature, the catalyst is 5-(3,5-bis(trifluoromethyl)phenyl)-1H-tetrazole (8) and the reaction time is 30 min. The resulting crude phosphoramidite product (36) had a purity of 97.1% and could be purified easily by flash chromatography to result in a phosphoramidite of 99.6% purity (FIG. 5) in excellent yield. As readily apparent to those skilled in the art the method can be easily adopted without much experimentation to any other nucleoside comprising a hydroxyl group.

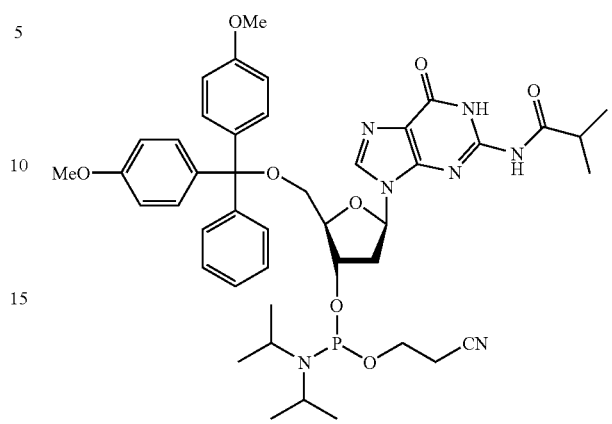

(36)

Additional advantages and novel features of this invention will become apparent to those skilled in the art upon examination of the examples thereof provided below, which should not be construed as limiting the appended claims.

EXAMPLES

The following examples are provided for illustrative purposes only and are not intended to limit the scope of the invention.

Example 1

Solubility and Acidity of 5-Substituted 1H-tetrazoles

Solid tetrazole derivatives (0.5 to 2 mmol) were incubated with acetonitrile (1 ml) at 25° C. in a shaker equipped with a thermostat overnight to result in saturated solutions of tetrazole derivatives which contained residual undissolved solid material. The suspensions were left without shaking at 25° C. until the solid material settled completely. An aliquot of the respective solutions (0.50 ml) was separated from the solid material and diluted with a mixture of acetonitrile and water (1/1, v/v, 20 ml). The resulting solution was titrated with NaOH solution (0.100 M, 10 ml) while the pH was measured with a glass electrode. The pH was recorded against the consumption of NaOH solution and the solubility and the pKa-value of the respective tetrazole derivative were calculated from the inflexion points of the corresponding titration curve. The results are set forth in Table 2.

TABLE 2

Solubility and acidity of 5-substituted 1H-tetrazoles

| Compound | Acidity pKa | Solubility (mol/ltr.) |
|---|---|---|
| 5-Phenyl-1H-tetrazole | 4.8 | 0.08 |
| 5-(3,5-Bis(trifluoromethyl)phenyl)-1H-tetrazole | 3.4 | 0.94 |
| 5-Ethylthio-1H-tetrazole | 4.2 | 1.52 |
| 5-Benzylthio-1H-tetrazole | 4.2 | 0.44 |

Example 2

Miscibility of Activator Solutions with Deblock- and Capping-Solutions

Solutions of tetrazole derivatives in acetonitrile were mixed with either deblock solution (3% trichloroacetic acid in dichloromethane, w/v), a mixture of Cap A and Cap B solution (1/1, v/v, Cap A=10% acetic anhydride in THF (v/v), Cap B=10% pyridine plus 10% n-methylimidazole in THF (v/v)), or a mixture of Fast Cap A and Cap B solution (1/1, v/v, Fast Cap A=5% (4-tert-butylphenoxy)acetic acid anhydride in THF (w/v), Cap B=10% pyridine plus 10% N-methylimidazole in THF (v/v)) in ratios of 1/9, 1/1 and 9/1, v/v. The resulting mixtures were visually inspected for the presence of precipitates. The results are set forth in Table 3.

TABLE 3

Miscibility of activator solutions with deblock- and capping-solutions

| Activator solution, acetonitrile as solvent | mixed with | observation |
|---|---|---|
| 0.45 M 1H-Tetrazole | Deblock | clear solution |
| | Cap A + Cap B | clear solution |
| | Fast Cap A + Cap B | clear solution |
| 0.5 M 4,5-Dicyanoimidazole | Deblock | ratio 9/1: clear solution |
| | | ratio 1/1: formation of solid particles which settle at the bottom of the tube |
| | | ratio 1/9: formation of a voluminous precipitate |
| | Cap A + Cap B | clear solution |
| | Fast Cap A + Cap B | clear solution |
| 0.5 M 5-(3,5-Bis(trifluoromethyl)-- phenyl)-1H-tetrazole | Deblock | clear solution |
| | Cap A + Cap B | clear solution |
| | Fast Cap A + Cap B | clear solution |

Example 3

Synthesis of the DNA Homosequence Oligonucleotide $dT_{10}$ (16) (SEQ ID NO:13)

The DNA oligonucleotide sequence $dT_{10}$ was synthesized using an ABI Expedite™ Model 8909 DNA/RNA synthesizer with commercial DMT-dT-phosphoramidite and commercial deblock-, capping- and oxidizer synthesis solutions at 1 µmol scale on a CPG 500 support. A 0.1 M solution of 5-(3,5-bis(trifluoromethyl)phenyl)-1H-tetrazole (8) was employed as activator solution. The synthesis was performed using the standard DNA synthesis protocol supplied by the manufacturer of the synthesizer in DMT-OFF mode. The oligonucleotide was cleaved from the support with 1 ml conc. aqueous ammonia (32%) for 45 minutes at room temperature and further incubated in the ammonia solution at 55° C. for 16 hours. The solution was cooled on ice and evaporated under vacuum centrifugation. The residue was dissolved in water and an aliquot was analyzed by anion-exchange HPLC on a Dionex DNAPac PA100 column (4×250 mm) eluting with a linear gradient from 20% to 50% buffer A in buffer B in 20.00 min at ambient temperature with a flow rate of 1.0 mL/min, detection at λ=260 nm, buffer A=25 mM Trizma hydrochloride/1 mM EDTA/1 M NaCl, pH 8.0, buffer B=25 mM Trizma hydrochloride/1 mM EDTA, pH 8.0. The purity of the oligonucleotide (retention time 10.2 min.) was 97.2% (average obtained from 2 independent synthesis runs). The identity of the oligonucleotide was confirmed by comparing the chromatogram with a chromatogram of the same sequence which was prepared employing a commercial activator (0.25 M DCI solution in acetonitrile).

Example 4

Synthesis of DNA Heterosequence Oligonucleotides (17) to (22)

The DNA oligonucleotides (17) to (22) were synthesized using an ABI Expedite™ Model 8909 DNA/RNA synthesizer with commercial nucleoside phosphoramidites dT, dA(bz), dG(ib) and dC(tac) ((4-tert-butylphenoxy)acetyl protection) and commercial deblock-, capping- and oxidizer synthesis solutions at 1 µmol scale on a CPG 500 support (for 22- to 35-mers) or a CPG 1000 support (51- and 103-mer). A 0.1 M solution of 5-(3,5-bis(trifluoromethyl)phenyl)-1H-tetrazole (8) was employed as activator solution. The synthesis was performed using the standard DNA synthesis protocol supplied by the manufacturer of the synthesizer in DMT-OFF mode. The oligonucleotides were cleaved from the support with 1 ml AMA (conc. aqueous ammonia (32%)/40% aqueous methylamine) for 30 minutes at room temperature and further incubated in the AMA solution at 65° C. for 25 minutes. The solutions were cooled on ice and evaporated under vacuum centrifugation. The residues were dissolved in water and aliquots were measured by UV spectroscopy to obtain the yields of the crude oligonucleotides. The oligonucleotides were precipitated through the addition of 3 M sodium acetate solution (11 µl per 100 µl solution, pH 5.5) and isopropanol (333 µl per 100 µl solution), mixing and incubation for 90 minutes at ambient temperature. The suspensions were centrifuged at maximum speed in a microcentrifuge for 10 minutes and the resulting supernatants were discarded. The remaining pellets were mixed with 70% ethanol in water (300 µl per 100 µl original solution) and incubated for 60 minutes at −20° C. The suspensions were centrifuged at maximum speed in a microcentrifuge for 2 minutes and the resulting supernatants were discarded. The remaining pellets were dissolved in water and aliquots were analyzed by anion-exchange HPLC on a Dionex DNAPac PA100 column (4×250 mm) eluting with a linear gradient of buffer A in buffer B within 30.00 min at 75° C. with a flow rate of 1.0 mL/min, detection at λ=260 nm, gradient for oligonucleotides up to 30-mers 30% to 90% buffer A in buffer B, gradient for longer oligonucleotides 40% to 90% buffer A in buffer B, buffer A=25 mM Trizma hydrochloride/1 mM EDTA/1 M NaCl, pH 8.0, buffer B=25 mM Trizma hydrochloride/1 mM EDTA, pH 8.0. The 22-mer to 51-mer oligonucleotides were further characterized by MALDI-TOF mass spectrometry and their identity was confirmed by the observed mass. The results are set forth in Table 1.

Example 5

Determination of the Average Coupling Efficiency in a Synthesis of the DNA Oligonucleotide (17)

The synthesis of the oligonucleotide (17) (22-mer) was repeated twice as described in Example 4, but at a scale of 0.2 µmol. The synthesizer effluents from the deblocking reaction which contained the cleaved DMT-moieties were collected in the 7th, 8th, 17th and 18th cycle in 10 ml volumetric flasks. The volumes of the obtained solutions were adjusted to 10.0 ml with deblock solution (3% trichloroacetic acid in dichloromethane) and the resulting solutions were analysed by VIS spectroscopy at 480 nm. The absorbances recorded from the 7th and 8th synthesis cycle were averaged to give a result Abs1 and the absorbances recorded from the 17th and 18th synthesis cycle were averaged to give a result Abs2. The coupling efficiency was calculated as the 10th root of the ratio of Abs2 to Abs1. The result was 99.3% coupling efficiency in the first synthesis run and 99.1% coupling efficiency in the second synthesis run.

Example 6

Synthesis of DNA Heterosequence Oligonucleotide (17) with Shortened Coupling Times The DNA oligonucleotide (17) was synthesized using an ABI Expedite™ Model 8909 DNA/RNA synthesizer with commercial nucleoside phosphoramidites dT, dA(bz), dG(ib) and dC(bz) and commercial deblock-, capping- and oxidizer synthesis solutions at 0.2 μmol scale on a CPG 500 support. A 0.1 M solution of 5-(3,5-bis(trifluoromethyl)phenyl)-1H-tetrazole (8) was employed as activator solution. The synthesis was performed 4 times using the standard DNA synthesis protocol supplied by the manufacturer of the synthesizer in DMT-OFF mode, except for the coupling routines of the coupling reactions, which had shortened coupling times of 10 seconds length in 2 of the syntheses and of 15 seconds length in the other 2 syntheses. The oligonucleotides were cleaved from the support with conc. aqueous ammonia (32%) for 30 minutes at ambient temperature and incubated in the resulting ammonia solution for 16 hours at 55° C. The solutions were cooled on ice and evaporated under vacuum centrifugation. The residues were dissolved in water and aliquots were analysed by anion-exchange HPLC as described in Example 4. All chromatograms had a main peak corresponding to oligonucleotide (17) with integrals of 59.6% and 59.5% for the synthesis that were conducted with 10 seconds coupling time and integrals of 58.2% and 58.6% for the synthesis that were conducted with 15 seconds coupling time.

Example 7

Synthesis of DNA Heterosequence Oligonucleotide (22) with Shortened Coupling Time The DNA oligonucleotide (21) was synthesized using an ABI Expedite™ Model 8909 DNA/RNA synthesizer with commercial nucleoside phosphoramidites dT, dA(bz), dG(ib) and dC(bz) and commercial deblock-, capping- and oxidizer synthesis solutions at 0.2 μmol scale on a CPG 1000 support. A 0.1 M solution of 5-(3,5-bis(trifluoromethyl)phenyl)-1H-tetrazole (8) was employed as activator solution. The synthesis was performed using the standard DNA synthesis protocol supplied by the manufacturer of the synthesizer in DMT-OFF mode, except for the coupling routines of the coupling reactions, which had shortened coupling times of 15 sec. length. The oligonucleotide was isolated as described in Example 6 and analysed by anion-exchange HPLC as described in Example 4. The chromatograms had a main peak corresponding to oligonucleotide (21) with an integral of 45.9%.

Example 8

Coupling Reaction of DMT-rA(tac)si-amidite (23) with dT-si (24) in a NMR Tube

A Varian Mercury 300 plus NMR-spectrometer was used in the following NMR-Measurements.

Stock solutions of the RNA nucleoside phosphoramidite DMT-rA(tac)si-amidite (23) (1.00 g in 1.25 ml, 0.745 M, solution 1), the nucleoside dT-si (24) (0.332 g in 1.25 ml, 0.745 M, solution 2), and the activators 5-(3,5-bis(trifluoromethyl)phenyl)-1H-tetrazole (8) (0.263 g in 1.00 ml, 0.936 M, solution 3) and ETT (0.121 g in 1.00 ml, 0.931 M, solution 4) were prepared in anhydrous deuterated acetonitrile. Solution 1 (250 μl) and solution 2 (300 μl) were mixed in predried 5 mm diameter NMR tubes. A $^{31}$P-NMR spectrum of the mixture displayed 2 signals at 150.6 ppm (40.6 area %) and 149.3 ppm (59.4 area %). One of the activator solutions (either solution 3 or solution 4, 400 μl) was added and $^{31}$P-NMR spectra of the resulting mixtures were recorded at ambient temperature using 8 pulses per spectrum (recording time 23 sec. per spectrum). The signals of the amidite educt (23) (150.6 and 149.3 ppm) and the product dinucleotide (25) (140.4 and 139.9 ppm) were integrated and the conversion rate of the amidite was calculated as conversion (%)=100× integral (product)/(integral educt+integral product). The results are set forth in Table 4 and FIG. 2.

TABLE 4

Coupling of Compound (23) and (24)

| Time (sec.) | Activator (8) Conversion (%) | Activator ETT Conversion (%) |
|---|---|---|
| 90 | 73 | 64 |
| 150 | 81 | 75 |
| 180 | 79 | 78 |
| 240 | 94 | 82 |
| 300 | 100 | 87 |
| 480 |  | 91 |
| 600 |  | 96 |
| 720 |  | 96 |
| 840 |  | 97 |
| 1020 |  | 100 |

Example 9

Investigation of Coupling Time Versus Coupling Efficiency for DMT-rC(tac)si-amidite (26) on a Solid Support The DNA oligonucleotide sequence dT$_6$ was synthesized using an ABI Expedite™ Model 8909 DNA/RNA synthesizer with commercial dT-phosphoramidite and commercial synthesis solutions at 15 μmol scale on a CPG 500 support. The synthesis was performed using the standard DNA synthesis protocol supplied by the manufacturer of the synthesizer in DMT-ON mode. The support with the bound oligonucleotide was removed from the synthesis column and distributed into standard plastic synthesis columns suitable for oligonucleotide synthesis at 1 μmol scale (30 mg CPG per column, approximately 1 μmol support-bound oligonucleotide). The columns were installed in the Model 8909 instrument and subjected to a single chain elongation cycle wherein DMT-rC(tac)si-amidite (26) was employed in the coupling reaction to result in the model oligonucleotide 5'-rCdT$_6$-3'. The RNA synthesis protocol as supplied by the manufacturer of the instrument was applied in DMT-OFF mode except for the coupling routine, which was modified with respect to the coupling time in order to allow couplings of either 2 minutes, 4 minutes, 6 minutes, 8 minutes or 10 minutes length. The phosphoramidite (26) was applied at a concentration of 50 mg/ml in acetonitrile and 240 µl of this solution was used in each coupling reaction (12 mg, approximately 12 equiv. with respect to support-bound oligonucleotide). A 0.1 M solution of 5-(3,5-bis(trifluoromethyl)phenyl)-1H-tetrazole (8) was employed as activator solution. The support bound oligonucleotides were treated with concentrated aqueous ammonia (32%) for 2 hours at ambient temperature. The supernatant was removed from the support by pipetting and evaporated under vacuum centrifugation. The residue was dissolved in 1 ml water to result in a solution of the oligonucleotide 5'-rCdT$_6$-3' wherein the cytidine residue carries a 2'-tert-butyldimethylsilyl protective group. An aliquot of the solution was analysed by reversed phase HPLC on a Waters XTerra MS C18 column (4.6×50 mm) eluting with a linear gradient from 5% to 100% acetonitrile in 100 mM triethylammonium acetate buffer pH 7.0 in 15.00 minutes with a flow rate of 1.0 mL/min, detection at λ=260 nm, retention time of dT$_6$ 9.99 minutes, retention time of 5'-rCdT$_6$-3' 14.35 min). The coupling efficiency of DMT-rC(tac)si-amidite (26) was calculated from the ratio of the signal area of the oligonucleotide 5'-rCdT$_6$-3' to the sum of the signal areas of the oligonucleotides dT$_6$ and 5'-rCdT$_6$-3'. The results are set forth in Table 5.

TABLE 5

Coupling Time versus Coupling Efficiency

| Coupling time (min.) | dT$_6$ (Area %) | 5'-rCdT$_6$-3' (Area %) | Coupling efficiency (%) |
|---|---|---|---|
| 2 | 15.50 | 53.14 | 77.4 |
| 4 | 2.85 | 65.60 | 91.5 |
| 6 | 1.05 | 67.24 | 98.5 |
| 8 | 0.88 | 65.35 | 98.7 |
| 10 | 0.64 | 51.51 | 98.8 |

Example 10

Synthesis of the RNA Oligonucleotide 5'-rU$_9$dT-3' (27)

The RNA oligonucleotide 5'-rU$_9$dT-3' (27) was synthesized using an ABI Expedite™ Model 8909 DNA/RNA synthesizer with commercial nucleoside phosphoramidite rU and commercial deblock-, capping- and oxidizer synthesis solutions at 1 µmol scale on a CPG 500 supports loaded with dT. A 0.1 M solution of 5-(3,5-bis(trifluoromethyl)phenyl)-1H-tetrazole (8) was employed as activator solution and Fast Cap A solution (5% (4-tert-butylphenoxy)acetic acid anhydride in THF, w/v, was applied as Cap A solution. The synthesis was performed using the standard RNA protocol supplied by the manufacturer of the synthesizer in DMT-OFF mode. The CPG support was removed from the synthesis column and incubated in 1 ml conc. aqueous ammonia (32%)/ethanol 3/1, v/v at 55° C. for 15 minutes. The mixture was cooled on ice and the supernatant was transferred to a separate vial and evaporated under vacuum centrifugation. The CPG support was washed with 1 ml of a mixture of water/ethanol/acetonitrile 3/1/1, v/v, and the washing solution was combined with the oligonucleotide residue and evaporated under vacuum centrifugation. The dried residue was incubated in 0.5 ml 1 M tetrabutylammonium fluoride solution in THF overnight. The solution was mixed with 1 ml of 1 M TEAA buffer pH 7.0 and concentrated to a volume of approximately. 1 ml under vacuum centrifugation. The mixture was desalted on a small Sephadex G25 column (NAP-10 column, elution with water). Respective column fractions were collected, evaporated to dryness under vacuum centrifugation and redissolved in 1.00 ml water. An aliquot of the oligonucleotide solution was measured by UV spectroscopy to obtain the yield of the crude oligonucleotide which was 51 OD. Another aliquot was analysed by reversed phase HPLC on a Waters XTerra MS C18 column (2.5×50 mm) eluting with a linear gradient from 0% to 66% buffer A in buffer B within 40.00 min. at 60° C. with a flow rate of 0.5 mL/min, detection at λ=260 nm, buffer A=0.1M TEAA-buffer with 30 vol % acetonitrile, buffer B=0.1 M TEAA-buffer with 5 vol % acetonitrile, and also analysed by anion-exchange HPLC on a Dionex DNAPac PA100 column (4×250 mm) eluting with a linear gradient from 30% to 90% buffer A in buffer B within 30.00 minutes at 75° C. with a flow rate of 1.0 mL/min, detection at λ=260 nm, buffer A=25 mM Trizma hydrochloride/1 mM EDTA/1 M NaCl, pH 8.0, buffer B=25 mM Trizma hydrochloride/1 mM EDTA, pH 8.0. The oligonucleotide was further characterized by MALDI-TOF mass spectrometry. The purity of the oligonucleotide was 97.8% by reversed phase HPLC and 90.5% by anion-exchange HPLC, MALDI-TOF mass observed m/z 3000, calculated m/z 2998.

Example 11

Synthesis of the RNA Heterosequence Oligonucleotide (28)

The RNA oligonucleotide sequence 5'-r(UAC-GUA-CGU-ACG)-3' (28) was synthesized as described for the oligonucleotide (27) in Example 10. Commercial nucleoside phosphoramidites rU, rA(tac), rG(tac) and rC(tac) ((4-tert-butylphenoxy)acetyl protection) were employed at 1 µmol scale on a CPG 500 support loaded with rG(tac). A 0.1 M solution of 5-(3,5-bis(trifluoromethyl)phenyl)-1H-tetrazole (8) was employed as activator solution and Fast Cap A solution (5% (4-tert-butylphenoxy)acetic acid anhydride in THF, w/v, was applied as Cap A solution. 34 OD of the crude oligonucleotide (28) were obtained and aliquots were analysed as described in Example 10. The purity of the oligonucleotide was 88.7% by reversed phase HPLC and 77.2% by anion-exchange HPLC, MALDI-TOF mass observed m/z 3794, calculated m/z 3795.

Example 12

Synthesis of 2'-O-methyl RNA Oligonucleotides (29) and (30)

The 2'-O-methyl RNA oligonucleotide sequences 5'-r(GUG-UGU-GUG-UGU-GUG-UGU-GU)-3' (29) (SEQ ID NO:10) and 5'-r(CGC-UCA-UCU-UCA-AGU-CCA-CCC-U)-3' (30) (SEQ ID NO:12) wherein all nucleosides are 2'-O-methyl-nucleosides were synthesized using an ABI Expedite™ Model 8909 DNA/RNA synthesizer with commercial nucleoside phosphoramidites 2'-O-methyl-rU, 2'-O-methyl-rA(bz), 2'-O-methyl-rG(ib) and 2'-O-methyl-rC(tac) ((4-tert-butylphenoxy)acetyl protection) and commercial deblock-, capping- and oxidizer synthesis solutions at 1 µmol scale on a CPG 500 support loaded with the respective 2'-O-methyl nucleoside. A 0.1 M solution of 5-(3,5-bis(trifluoromethyl) phenyl)-1H-tetrazole (8) was employed as activator solution. The synthesis was performed using the standard RNA protocol supplied by the manufacturer of the synthesizer in DMT- OFF mode, except for the coupling routines of the coupling reactions, which had shortened coupling times of 6 min. length. The oligonucleotides were cleaved from the support with 1 ml AMA (conc. aqueous ammonia (32%)/40% aqueous methylamine) for 30 minutes at room temperature and further incubated in the AMA solution at 65° C. for 25 minutes. The solutions were cooled on ice and evaporated under vacuum centrifugation. The residues were dissolved in water and aliquots were measured by UV spectroscopy to obtain the yields of the crude oligonucleotides. The oligonucleotides were precipitated through the addition of 3 M sodium acetate solution (11 µl per 100 µl solution, pH 5.5) and isopropanol (333 µl per 100 µl solution), mixing and incubation for 90 minutes at ambient temperature. The suspensions were centrifuged at maximum speed in a microcentrifuge for 10 min. and the resulting supernatants were discarded. The remaining pellets were mixed with 70% ethanol in water (300 µl per 100 µl original solution) and incubated for 60 minutes at −20° C. The suspensions were centrifuged at maximum speed in a microcentrifuge for 2 minutes and the resulting supernatants were discarded. The remaining pellets were dissolved in water and aliquots were analyzed by anion-exchange HPLC on a Dionex DNAPac PA100 column (4×250 mm) eluting with a linear gradient from 30% to 90% buffer A in buffer B within 30.00 minutes at 75° C. with a flow rate of 1.0 mL/min, detection at $\lambda$=260 nm, buffer A=25 mM Trizma hydrochloride/1 mM EDTA/1 M NaCl, pH 8.0, buffer B=25 mM Trizma hydrochloride/1 mM EDTA, pH 8.0. Oligonucleotide (29) had a purity of 57.7% (retention time 12.1 min.) and oligonucleotide (30) had a purity of 60.8% (retention time 12.5 min.).

Example 13

Synthesis of the DNA Oligonucleotides $dT_{10}$ (16) (SEQ ID NO:13), $dA_{10}$ (32) SEQ ID NO:14), $dC_{10}$ (33) (SEQ ID NO:6) and 5'-d(GT)$_5$ (34) (SEQ ID NO:11) with Prolonged Coupling Time The DNA oligonucleotides (31) to (34) were synthesized using an ABI Expedite™ Model 8909 DNA/RNA synthesizer with commercial nucleoside phosphoramidites dT, dA(bz), dG(ib) and dC(bz) and commercial deblock-, capping- and oxidizer synthesis solutions on respective CPG 500 supports loaded with dT, dA(bz) or dC(bz). A 0.1 M solution of 5-(3, 5-bis(trifluoromethyl)phenyl)-1H-tetrazole (8) was employed as activator solution. Each synthesis was performed twice in DMT-OFF mode using the standard RNA synthesis protocol supplied by the manufacturer of the synthesizer (coupling time approximately 12 minutes) at 0.2 µmol scale in the first synthesis and the standard DNA synthesis protocol supplied by the manufacturer of the synthesizer (coupling time approximately 90 seconds) at 1 µmol scale in the second synthesis. The oligonucleotides were cleaved from the support with conc. aqueous ammonia (32%) for 30 minutes at ambient temperature and incubated in the resulting ammonia solution for 16 hours at 55° C. The solutions were cooled on ice and evaporated under vacuum centrifugation. The residues were dissolved in water and aliquots were analysed by anion-exchange HPLC in non-desalted form under conditions as described in Example 4. The results are set forth in Table 6.

TABLE 6

Synthesis of Oligonucleotides (31)-(34)

| | Sequence | Coupling Time | Purity (%) | n + 1-mer (%) |
|---|---|---|---|---|
| (31) | $dT_{10}$ | 90 sec. | 85.3 | 0.6 |
| (31) | $dT_{10}$ | 12 min. | 87.9 | 1.0 |
| (32) | $dA(bz)_{10}$ | 90 sec. | 71.3 | 0.5 |
| (32) | $dA(bz)_{10}$ | 12 min. | 75.4 | 0.7 |
| (33) | $dC(bz)_{10}$ | 90 sec. | 79.0 | not detected |
| (33) | $dC(bz)_{10}$ | 12 min. | 77.3 | 0.1 |
| (34) | 5'-d(GT)$_5$-3' | 90 sec. | 89.2 | not detected |
| (34) | 5'-d(GT)$_5$-3' | 12 min. | 88.6 | 0.3 |

Example 14

Hygroscopy of 5-(3,5-bis(trifluoromethyl)phenyl)-1H-tetrazole (8)

A carefully dried sample of compound (8) (50.013 g) was deposited in a desiccator which contained a saturated solution of sodium chloride (75-76% relative humidity at 15-25° C.) for 8 days at ambient temperature. The sample gained less than 3 mg weight.

Example 15

Synthesis of 5-(3,5-bis(trifluoromethyl)phenyl)-1H-tetrazole (8)

Anhydrous zinc bromide (93.5 g, 415 mmol, 0.99 equiv.), sodium azide (29.8 g, 458 mmol, 1.1 equiv.) and water (750 ml) were added to 3,5-bis(trifluoromethyl)benzonitrile (100.0 g, 418 mmol, 1.00 equiv.). The resulting suspension was stirred for 10 days at ambient temperature. The completion of the reaction was confirmed by reversed phase HPLC on a Waters Novapak C18 column (3.9×150 mm) eluting with a linear gradient from 40% to 100% acetonitrile in 250 mM triethylammonium acetate buffer pH 6.5 in 15.00 minutes with a flow rate of 1.0 mL/min, detection at $\lambda$=270 nm, product retention time 2.0 min., educt retention time 6.5 min. Ethyl acetate (3.8 ltr.) and 10% citric acid in water were added and the resulting mixture was vigorously stirred for 15 minutes. The aqueous phase was separated and extracted with ethyl acetate (2×900 ml). The organic phases were combined and evaporated to dryness. The resulting solid was stirred in aqueous NaOH solution (0.25 M, 3.8 ltr.) for 30 minutes to give a suspension, which was filtered. The filtrate was acidified with aqueous HCl (375 ml conc. hydrochloric acid and 375 ml water) which caused the product to precipitate as a fine white powder. The product was collected by filtration after one hour, washed with cold hexanes (100 ml) and dried in a desiccator under vacuum, yield 72.7 g (62%) of compound (8) as white crystalline powder. The purified product had a purity of 100% by reversed phase HPLC as depicted in FIG. 4. $^1$H NMR (300 MHz, d$_6$-DMSO) δ 8.26 (s, 1H), 8.59 (s, 1H), m.p. 179° C. The product can be recrystallized from toluene.

Example 16

Synthesis of the DNA Oligonucleotides $dT_{10}$ (31), $dA_{10}$ (32) $dC_{10}$ (33) and 5'-d(GT)$_5$ (34) with Activator (8) in the Presence of N-methylimidazole The DNA oligonucleotides (31) to (34) were synthesized and analysed by anion-exchange HPLC as described in Example 13 except for the activator solution used in the synthesis which contained activator (8) (0.1 M) and N-methylimidazole (0.01 M). The crude undesalted oligonucleotides were obtained in 90.4% purity in case of oligomer (31), 87.9% purity in case of oligomer (32), 85.7% purity in case of oligomer (33) and 97.5% purity in case of oligomer (34).

Example 17

Synthesis of DMT-dG(ib)-amidite (36)

Figure 5:
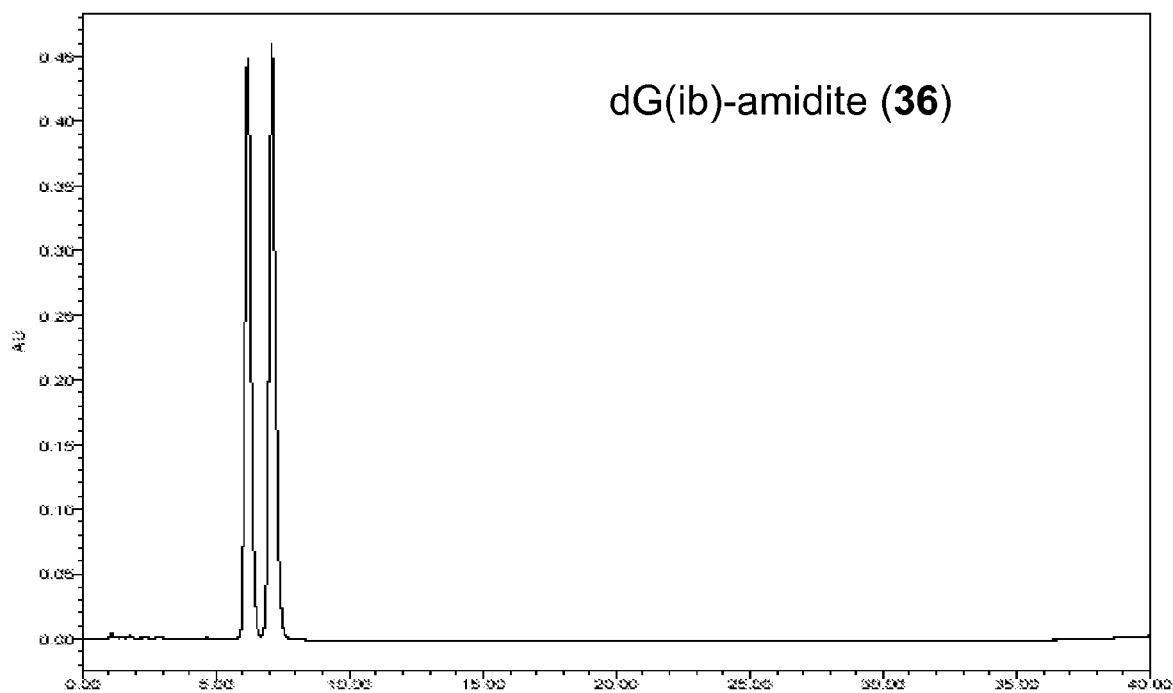
FIG. 5 displays the reversed phase HPLC chromatogram of dG(ib)-amidite (36) synthesized in Example 17.

5'-O-Dimethoxytrityl-N-2-isobutyryldeoxyguanosine (10.0 g, 15.6 mmol) was dried by coevaporation with THF (100 ml) and dissolved in dichloromethane (50 ml). Bis(diisopropylamino)-2-cyanoethoxyphosphane (14) (5.17 g, 17.2 mmol, 1.10 equiv.) and a solution of 5-(3,5-bis(trifluoromethyl)phenyl)-1H-tetrazole (8) (2.21 g, 7.8 mmol, 0.50 equiv.) and diisopropylethylamine (2.7 ml, 2.00 g, 15.5 mmol, 1.0 equiv.) in dichloromethane (10 ml) were added sequentially and the resulting reaction mixture was stirred at ambient temperature for 30 min. The reaction mixture was extracted with 10% aqueous sodium carbonate solution (4 times, 100 ml each), the organic phase was dried over sodium sulfate, filtered and evaporated to dryness. The crude product was analyzed by reversed phase HPLC on a Waters Novapak C18 column (3.9×150 mm) eluting with a linear gradient from 60% to 100% acetonitrile in 250 mM triethylammonium acetate buffer pH 6.5 in 20.00 min with a flow rate of 2.0 mL/min, detection at λ=270 nm, retention time of (36) 6.2 min. and 7.2 min. (pair of diastereoisomers). The chromatogram displayed 13.1% signal area for (8) and 39.49%/44.89% signal area for the product diastereoisomers (product purity excluding activator (8) 97.1%). The product was purified by flash chromatography (50-100% ethyl acetate in hexanes, gradient elution) yielding 10.0 g (76%) of amidite (36) as a white amorphous powder. The purified product had a purity of 99.6% by reversed phase HPLC as depicted in FIG. 5 (HPLC conditions as described above). $^{31}$P NMR (121.47 MHz, CDCl$_3$) δ 148.6/149.1 ppm.

What is claimed is:

1. A method for the synthesis of oligonucleotides pursuant to the phosphoramidite approach, the method comprising: reacting, in a coupling reaction, a nucleotide monomer or oligomer phosphoramidite with a nucleoside monomer or oligonucleotide in a solvent in the presence of a catalyst wherein the catalyst is an aryl-substituted 5-phenyl-1H-tetrazole and wherein at least one substituents at the phenyl ring of the aryl-substituted 5-phenyl-1H-tetrazole catalyst is a perfluoroalkyl substituent.

2. The method of claim 1, wherein the aryl-substituted 5-phenyl-1H-tetrazole is characterized by having a solubility in the solvent of the coupling reactions of at least about 0.5 mole per litre at a temperature of about 25° C.

3. The method of claim 1, wherein the oligonucleotide synthesis is conducted as solid phase oligonucleotide synthesis.

4. The method of claim 1, wherein the solvent of the coupling reactions is acetonitrile.

5. The method of claim 1, wherein the synthesized oligonucleotide is an RNA oligonucleotide.

6. The method of claim 1, wherein the aryl-substituted 5-phenyl-1H-tetrazole is 5-(3,5-bis(trifluoromethyl)phenyl)-1H-tetrazole.

7. The method of claim 6, wherein the oligonucleotide synthesis is conducted as solid phase oligonucleotide synthesis.

8. The method of claim 6, wherein the solvent of the coupling reactions is acetonitrile.

9. The method of claim 6, wherein the synthesized oligonucleotide is an RNA oligonucleotide.

10. The method of claim 9, wherein the employed phosphoramidites are 2'-O-protected with tert-butyldimethylsilyl protective groups.

11. The method of claim 10, wherein the coupling reactions are conducted with a maximum coupling time of about 5 minutes.

12. The method of claim 6, wherein the synthesized oligonucleotide is a DNA oligonucleotide.

13. The method of claim 12, wherein the coupling reactions are conducted with a maximum coupling time of about 15 seconds.

14. The method of claim 6, wherein the aryl-substituted 5-phenyl-1H-tetrazole reacts in the presence of a nucleophilic catalyst.

15. The method of claim 14, wherein the nucleophilic catalyst is N-methylimidazole.

16. The methods of claim 14, wherein the nucleophilic catalyst is in a molar ratio of between about 1:20 and about 1:3 with respect to the aryl-substituted 5-phenyl-1H-tetrazole.

* * * * *